US009538982B2

(12) United States Patent
Anthony et al.

(10) Patent No.: US 9,538,982 B2
(45) Date of Patent: Jan. 10, 2017

(54) USER INTERFACE FOR ULTRASOUND SCANNING SYSTEM

(71) Applicant: Massachusetts Institute of Technology, Cambridge, MA (US)

(72) Inventors: Brian W. Anthony, Cambridge, MA (US); Shih-Yu Sun, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 34 days.

(21) Appl. No.: 13/798,899

(22) Filed: Mar. 13, 2013

(65) Prior Publication Data
US 2013/0296707 A1   Nov. 7, 2013

Related U.S. Application Data

(60) Provisional application No. 61/642,315, filed on May 3, 2012.

(51) Int. Cl.
*A61B 8/08* (2006.01)
*A61B 8/00* (2006.01)
*A61B 8/13* (2006.01)

(52) U.S. Cl.
CPC ............... *A61B 8/4254* (2013.01); *A61B 8/13* (2013.01); *A61B 8/4209* (2013.01); *A61B 8/4245* (2013.01); *A61B 8/4263* (2013.01); *A61B 8/4444* (2013.01); *A61B 8/4472* (2013.01); *A61B 8/461* (2013.01); *A61B 8/463* (2013.01); *A61B 8/483* (2013.01); *A61B 8/54* (2013.01)

(58) Field of Classification Search
CPC .............. A61B 8/42; A61B 2019/5297; A61B 2019/5291;A61B 2019/507; A61B 8/4254; A61B 8/4209; A61B 8/4245; A61B 8/463; A61B 8/4263; A61B 8/4444; A61B 8/4472; A61B 8/483; A61B 8/54; A61B 8/13; A61B 8/461
USPC ........................................................ 600/459
See application file for complete search history.

(56) References Cited

U.S. PATENT DOCUMENTS

| 5,608,849 | A  | * | 3/1997  | King, Jr. ................... 345/419 |
| 6,500,119 | B1 | * | 12/2002 | West et al. ................. 600/437 |
| 7,597,664 | B2 |   | 10/2009 | Jones et al. |
| 8,328,725 | B2 | * | 12/2012 | Anthony .............. A61B 5/0048 600/459 |
| 8,333,704 | B2 | * | 12/2012 | Anthony .............. A61B 5/0048 600/459 |

(Continued)

OTHER PUBLICATIONS

Najafi et al., "Force Regulating Using Concepts of Haptic and Visual Force Feedbacks", 2011, Transactions of the Canadian Society for Mechanical Engineering, vol. 35, No. 2, 177-199.*

(Continued)

*Primary Examiner* — Long V Le
*Assistant Examiner* — Angela M Hoffa
(74) *Attorney, Agent, or Firm* — Strategic Patents, P.C.

(57) ABSTRACT

An ultrasound scanning system includes a graphical user interface that provides visually intuitive feedback to a user to assist the user in properly aligning an ultrasound scanner to a desired acquisition state. In addition to providing pose information, the feedback may direct the user as to a target contact force applied by the ultrasound scanner to a surface undergoing a scan.

25 Claims, 14 Drawing Sheets

(56) References Cited

U.S. PATENT DOCUMENTS

| | | | | |
|---|---|---|---|---|
| 8,382,671 B2* | 2/2013 | Anthony | ............... | A61B 5/0048 600/437 |
| 8,753,278 B2* | 6/2014 | Stoll | ............... | A61B 8/0825 600/438 |
| 8,768,018 B2* | 7/2014 | Ishikawa | ............... | G06T 3/0093 382/128 |
| 9,456,800 B2* | 10/2016 | Anthony | ............... | A61B 8/4209 |
| 2004/0254460 A1* | 12/2004 | Burcher | ............... | A61B 5/6843 600/437 |
| 2005/0015005 A1 | 1/2005 | Kockro | | |
| 2006/0085049 A1 | 4/2006 | Cory et al. | | |
| 2008/0208041 A1 | 8/2008 | Gilboa | | |
| 2009/0306509 A1 | 12/2009 | Pedersen et al. | | |
| 2009/0326318 A1* | 12/2009 | Tognaccini et al. | ............... | 600/104 |
| 2010/0222680 A1* | 9/2010 | Hamada | ............... | 600/443 |
| 2011/0152690 A1* | 6/2011 | Anthony | ............... | A61B 5/0048 600/459 |
| 2011/0166453 A1* | 7/2011 | Anthony | ............... | A61B 5/0048 600/443 |
| 2011/0172541 A1* | 7/2011 | Anthony | ............... | A61B 5/0048 600/459 |
| 2012/0172710 A1* | 7/2012 | Anthony | ............... | A61B 5/0048 600/411 |
| 2012/0316407 A1* | 12/2012 | Anthony | ............... | A61B 8/4209 600/301 |
| 2013/0317365 A1 | 11/2013 | Anthony et al. | | |
| 2014/0114193 A1* | 4/2014 | Anthony | ............... | A61B 8/4209 600/459 |

OTHER PUBLICATIONS

Stolka, Philipp J. et al., "5-DoF Trajectory Reconstruction for Handheld Ultrasound with Local Sensors", 2009 IEEE International Ultrasonics Symposium Proceedings, Sep. 23, 2009, pp. 1864-1867.

Poulsen, Carsten et al., "An Optical Registration Method for 3D Ultrasound Freehand Scanning", 2005 IEEE Ultrasonics Symposium, Sep. 21, 2005, pp. 1236-1240.

Stolka, Philipp J. et al., "Multi-DoF Probe Trajectory Reconstruction with Local Sensors for 2D-to3D Ultrasound", International Symposium on Biomedical Imaging 2010, Apr. 17, 2010, pp. 316-319.

Goldsmith, A. M. et al., "An Inertial-Optical Tracking System for Portable, Quantitative, 3D Ultrasound", 2008 IEEE International Ultrasonics Symposium Proceedings, Nov. 5, 2008, pp. 45-49.

"U.S. Appl. No. 13/886,981, Non-Final Office Action mailed Apr. 2, 2015", 25 pages.

"U.S. Appl. No. 13/886,981, Non-Final Office Action mailed Oct. 7, 2016", 14 pages.

* cited by examiner

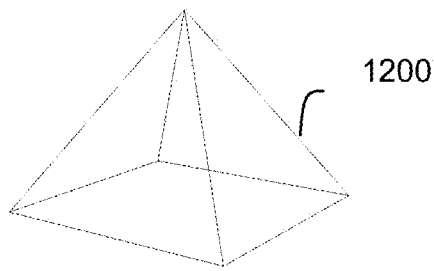
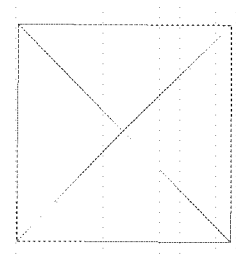
Fig. 12                     Fig. 13
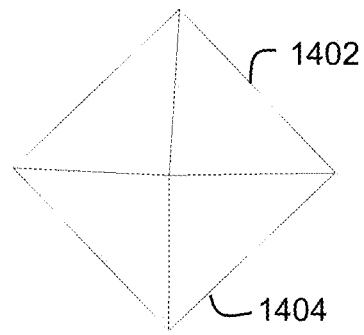
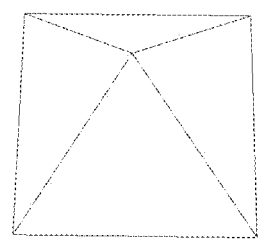
Fig. 14                     Fig. 15
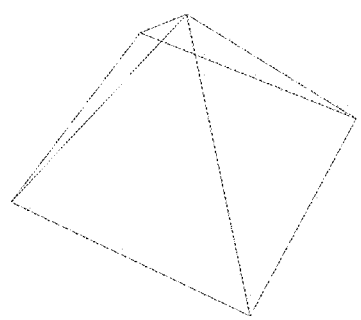
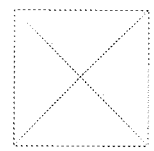
Fig. 16                     Fig. 17

USER INTERFACE FOR ULTRASOUND SCANNING SYSTEM

CROSS-REFERENCE TO RELATED APPLICATIONS

This application claims the benefit of U.S. App. No. 61/642,315 filed on May 3, 2012.

This application is related to U.S. patent application Ser. No. 12/972,461 filed on Dec. 18, 2010 and U.S. application Ser. No. 13/342,627 filed on Jan. 3, 2012. Each of the foregoing applications is hereby incorporated by reference in its entirety.

FIELD OF THE INVENTION

The invention generally relates to ultrasound imaging, and more particularly to visual feedback systems for steering an ultrasound probe to a predetermined acquisition state.

BACKGROUND

While medical ultrasound images can be quickly and cheaply obtained from a handheld ultrasound imaging device, this type of imaging generally suffers from a lack of accurate information concerning the conditions under which the scan was captured. As a result, two-dimensional ultrasound images from handheld probes are generally limited in use to a qualitative evaluation of the imaged tissue.

There remains a need for tools and techniques to return an ultrasound imaging device to a previous or otherwise predetermined acquisition state that includes, e.g., a position, an orientation, a rotation and/or an instantaneous contact force.

SUMMARY

An ultrasound scanning system includes a graphical user interface that provides visually intuitive feedback to a user to assist the user in properly aligning an ultrasound scanner to a desired acquisition state. In addition to providing pose information, the feedback may direct the user as to a target contact force applied by the ultrasound scanner to a surface undergoing a scan.

BRIEF DESCRIPTION OF THE FIGURES

The invention and the following detailed description of certain embodiments thereof may be understood by reference to the following figures:

FIG. 12 shows a pyramid.

FIG. 13 shows a pyramid.

FIG. 14 shows a pyramid.

FIG. 15 shows a pyramid.

FIG. 16 shows a pyramid.

FIG. 17 shows a pyramid.

DETAILED DESCRIPTION

The techniques described herein enable real-time control of the contact force between an ultrasound probe and a target, such as a patient's body. This allows ultrasound technicians to take fixed- or variably-controlled-contact-force ultrasound measurements of the target, as desired. This also facilitates measurement, tracking, and/or control of the contact force in a manner that permits enhanced, quantitative analysis and subsequent processing of ultrasound image data.

Figure 1:
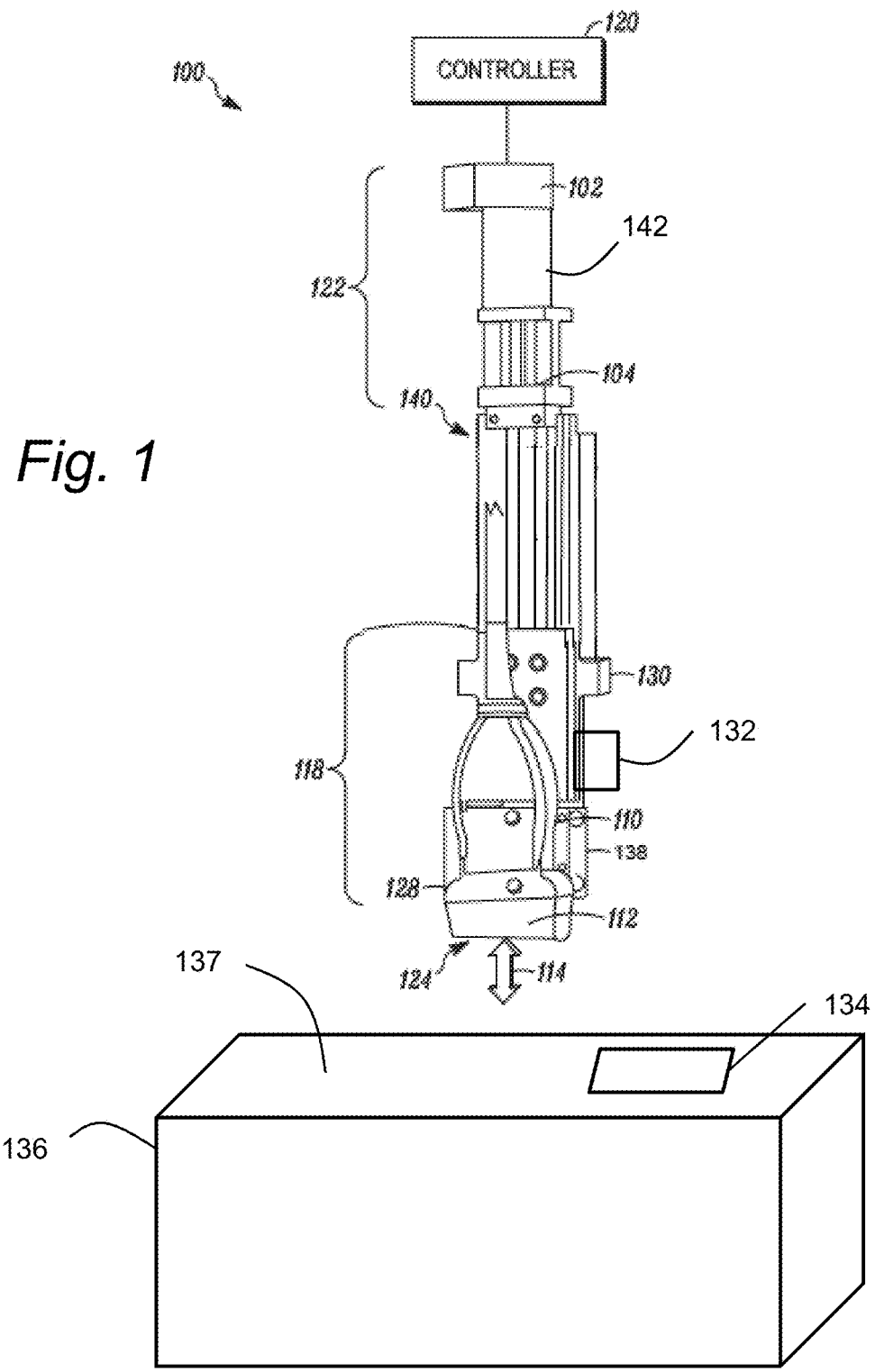
FIG. 1 is a perspective view of a handheld ultrasound probe control device.

FIG. 1 is a perspective view of a handheld ultrasound probe control device. The device 100 may include a frame 118 adapted to receive a probe 112, a linear drive system 122 that translates the frame 118 along an actuation axis 114, a sensor 110 such as a force sensor, a torque sensor, position sensor 142 or some combination of these, and a controller 120.

The probe 112 can be of any known type or construction. The probe 112 may, for example include a handheld ultrasound probe used for medical imaging or the like. More generally, the probe 112 may include any contact scanner or other device that can be employed in a manner that benefits from the systems and methods described herein. Thus, one advantage of the device 100 is that a standard off-the-shelf ultrasound medical probe can be retrofitted for use as a force-controlled ultrasound in a relatively inexpensive way; i.e., by mounting the probe 112 in the frame 118. Medical ultrasound devices come in a variety of shapes and sizes, and the frame 118 and other components may be adapted for a particular size/shape of probe 112, or may be adapted to accommodate a varying sizes and/or shapes. In another aspect, the probe 112 may be integrated into the frame 118 or otherwise permanently affixed to or in the frame 118.

In general, a probe 112 such as an ultrasound probe includes an ultrasound transducer 124. The construction of suitable ultrasound transducers is generally well known, and a detailed description is not required here. In one aspect, an ultrasound transducer includes piezoelectric crystals or similar means to generate ultrasound waves and/or detect incident ultrasound. More generally, any suitable arrangement for transmitting and/or receiving ultrasound may be used as the ultrasound transducer 124. Still more generally, other transceiving mechanisms or transducers may also or instead be used to support imaging modalities other than ultrasound.

The frame 118 may include any substantially rigid structure that receives and holds the probe 112 in a fixed position and orientation relative to the frame 118. The frame 118 may include an opening that allows an ultrasound transducer 124 of the probe 112 to contact a patient's skin or other surface through which ultrasound images are to be obtained. Although FIG. 1 shows the probe 112 held within the frame 118 between two plates (a front plate 128 bolted to a larger plate 130 on the frame 118) arranged to surround a handheld ultrasound probe and securely affix the probe to the frame 118, any suitable technique may also or instead be employed to secure the probe 112 in a fixed relationship to the frame 118. For example, the probe 112 may be secured with a press fit, hooks, screws, anchors, adhesives, magnets, or any combination of these and other fasteners. More generally, the frame 118 may include any structure or combination of structure suitable for securely retaining the probe 112 in a fixed positional relationship relative to the probe 112.

In one aspect, the frame 118 may be adapted for handheld use, and more particularly adapted for gripping by a technician in the same orientation as a conventional ultrasound probe. Without limitation, this may include a trunk 140 or the like for gripping by a user that extends axially away from the ultrasound transducer 124 and generally normal to the contact surface of the transducer 124. Stated alternatively, the trunk 140 may extend substantially parallel to the actuation axis 114 and be shaped and sized for gripping by a human hand. In this manner, the trunk 140 may be gripped by a user in the same manner and orientation as a typical handheld ultrasound probe. The linear drive system 122 may advantageously be axially aligned with the trunk 140 to permit a more compact design consistent with handheld use. That is, a ballscrew or similar linear actuator may be aligned to pass through the trunk 140 without diminishing or otherwise adversely affecting the range of linear actuation.

The linear drive system 122 may be mounted on the device 100 and may include a control input electronically coupled to the controller 120. The linear drive system 122 may be configured to translate the probe 112 along an actuation axis 114 in response to a control signal from the controller 120 to the control input of the linear drive system 122. Additionally, the linear drive system 122 may include a position sensor 142 to provide position information characterizing a position of the probe 112 along the actuation axis. The position may, for example, be a position relative to one or more travel limits of the linear drive system 122. Although the linear drive system 122 is depicted by way of example as a motor 102 and a linear actuator 104, any system capable of linearly moving the probe 112 can be employed. For example, the linear drive system 122 can include a mechanical actuator, hydraulic actuator, pneumatic actuator, piezoelectric actuator, electro-mechanical actuator, linear motor, telescoping linear actuator, ballscrew-driven linear actuator, and so on. More generally, any actuator or combination of actuators suitable for use within a grippable, handheld form factor such as the trunk 140 may be suitably employed as the linear drive system 122. In some implementations, the linear drive system 122 is configured to have a low backlash (e.g., less than 3 μm) or no backlash in order to improve positional accuracy and repeatability.

The ability of the probe 112 to travel along the actuation axis 114 permits the technician some flexibility in hand placement while using the device 100. In some implementations, the probe 112 can travel up to six centimeters along the actuation axis 114, although greater or lesser ranges of travel may be readily accommodated with suitable modifications to the linear actuator 104 and other components of the device 100.

The motor 102 may be electrically coupled to the controller 120 and mechanically coupled in a fixed positional relationship to the linear actuator 104. The motor 102 may be configured to drive the linear actuator 104 in response to control signals from the controller 120, as described more fully below. The motor 102 can include a servo motor, a DC stepper motor, a hydraulic pump, a pneumatic pump, and so on.

The sensor 110, which may include a force sensor and/or a torque sensor, may be mechanically coupled to the frame 118, such as in a fixed positional relationship to sense forces/torques applied to the frame 118. The sensor 110 may also be electronically coupled to the controller 120, and configured to sense a contact force between the probe 112 and a target surface (also referred to herein simply as a "target") such as a body from which ultrasound images are to be captured. As depicted, the sensor 110 may be positioned between the probe 112 and the back plate of the frame 118. Other deployments of the sensor 110 are possible, so long as the sensor 110 is capable of detecting the contact force (for a force sensor) between the probe 112 and the target surface. Embodiments of the sensor 110 may also or instead include a multi-axis force/torque sensor, a plurality of separate force and/or torque sensors, or the like.

The force sensor may be mechanically coupled to the ultrasound probe 112 and configured to obtain a pressure applied by the ultrasound probe 112 to the skin surface or a target 136. The force sensor may include a pressure transducer coupled to the ultrasound probe 112 and configured to sense an instantaneous contact force between the handheld ultrasound probe 112 and the skin.

The sensor 110 can provide output in any known form, and generally provides a signal indicative of forces and/or torques applied to the sensor 110. For example, the sensor 110 can produce analog output such as a voltage or current proportional to the force or torque detected. Alternatively, the sensor 110 may produce digital output indicative of the force or torque detected. Moreover, digital-to-analog or analog-to-digital converters (not shown) can be deployed at any point between the sensors and other components to convert between these modes. Similarly, the sensor 110 may provide radio signals (e.g., for wireless configurations), optical signals, or any other suitable output that can characterize forces and/or torques for use in the device 100 described herein.

The controller 120 generally includes processing circuitry to control operation of the device 100 as described herein. The controller 120 may receive signals from the sensor 110 indicative of force/torque and from the position sensor 142 of the linear drive system 122 indicative of the position of the probe 112 relative to the travel end points, and may generate a control signal to a control input of the linear drive system 122 (or directly to the linear actuator 104) for maintaining a given contact force between the ultrasound probe 112 and the target, as described more fully below. The controller 120 may include analog or digital circuitry, computer program code stored in a non-transitory computer-readable storage medium, and so on. Embodiments of the controller 120 may employ pure force control, impedance control, contact force-determined position control, and so on.

The controller 120 may be configured with preset limits relating to operational parameters such as force, torque, velocity, acceleration, position, current, etc. so as to immediately cut power from the linear drive system 122 when any of these operational parameters exceed the preset limits. In some implementations, these preset limits are determined based on the fragility of the target. For example, one set of preset limits may be selected where the target is a healthy human abdomen, another set of preset limits may be selected where the target is a human abdomen of an appendicitis patient, etc. In addition, preset limits for operational parameters may be adjusted to accommodate discontinuities such as initial surface contact or termination of an ultrasound scan (by breaking contact with a target surface).

In some implementations, the device 100 includes a servo-motor-driven ballscrew linear actuator comprising a MAXON servo motor (EC-Max #272768) (motor 102) driving an NSK MONOCARRIER compact ballscrew actuator (linear actuator 104). a MINI40 six-axis force/torque sensor (sensor 110) from ATI INDUSTRIAL AUTOMATION, which simultaneously monitors all three force and all three torque axes, may be mounted to the carriage of the actuator, and a TERASON 5 MHz ultrasound transducer (ultrasound transducer 124) may be mounted to the force/torque sensor.

The vector from a geometric origin of the sensor 110 to an endpoint at the probe 124 that contacts a patient can be used to map the forces and torques at the sensor 110 into the contact forces and torques seen at the probe/patient interface. In some implementations, it is possible to maintain a set contact force with a mean error of less than 0.2% and, in a closed-loop system, maintain a desired contact force with a mean steady state error of about 2.1%, and attain at least 20 Newtons of contact force. More generally, in one embodiment a steady state error of less than 3% was achieved for applied forces ranging from one to seven Newtons.

Other sensors (indicated generically as a second sensor 138) may be included without departing from the scope of this invention. For example, a second sensor 138 such as an orientation sensor or the like may be included, which may be operable to independently detect at least one of a position and an orientation of the device 100, such as to track location and/or orientation of the device 100 before, during, and after use. This data may help to further characterize operation of the device 100. A second sensor 138 such as a range or proximity detector may be employed to anticipate an approaching contact surface and place the device 100 in a state to begin an ultrasound scan. For example, a proximity sensor may be operable to detect a proximity of the ultrasound transducer 124 to a subject (e.g., the target surface). One or more inertial sensors may be included in the device 100. Suitable inertial sensors include, for example, inertial sensors based on MEMS technology such as accelerometers and gyroscopes, or any other device or combination of devices that measure motion. More generally, any of a variety of sensors known in the art may be used to augment or supplement operation of the device 100 as contemplated herein.

The ultrasound probe may further include a sensor for illuminating the skin surface when the handheld ultrasound probe is placed for use against the skin surface. For example, the sensor may be a lighting source mechanically coupled to the handheld ultrasound probe and positioned to illuminate the skin surface during use of the ultrasound probe. The lighting source may be part of the sensor system of the ultrasound probe or the lighting source may be a separate device directed toward the ultrasound probe. Suitable lighting sources include an LED light or any other light capable of illuminating the skin surface during ultrasound scanning.

Another sensor that may be included in the device 100 is a camera 132. The camera 132 may be positioned to record a digital image of the skin surface 136 during an ultrasound scan when the handheld ultrasound probe 112 is placed for use against the skin surface 137 of the target 136. The camera 132 also may be positioned to obtain a pose of the handheld ultrasound probe 112 as the ultrasound transducer 124 scans the target 136. The camera 132 may be mechanically coupled to the ultrasound transducer 124. In one aspect, the camera 132 may be rigidly mounted to the ultrasound transducer 124 and directed toward the skin surface 137 (when positioned for use) in order to capture images of the skin surface 137 and/or a target 134 adhered to the skin surface 137. In another aspect, the camera 132 may be mounted separate from the ultrasound probe 112 and directed toward an area of use of the ultrasound probe 112 so that the camera 132 can capture images of the ultrasound probe 112 in order to derive pose information directly from images of the ultrasound probe 112. Suitable cameras 132 may for example include any commercially available digital camera or digital video camera designed to capture images of sufficient quality for use as contemplated herein.

The ultrasound probe 112 may have an integral structure with various components coupled directly to a body thereof, or one or more of the various functions of one or more of the components of the ultrasound probe may be distributed among one or more independent devices. For example, the camera, the lighting source, and any other sensors may be integrated into the ultrasound probe or they may be separate from the ultrasound probe, along with suitable communications and control systems where coordination of function is desired between the probe and the external components.

The ultrasound probe 112 may be used to capture an ultrasound image of a target 136 through a skin surface 137. A fiducial marker 134 with predetermined dimensions may be applied to the skin surface 137 of the target 136 that is to be scanned by the ultrasound probe 112. The fiducial marker 134 may have any desired dimension or shape such as a square, a rectangle, a circle and/or any other regular, irregular, and/or random shape and/or patterns. In one embodiment, the fiducial marker 134 may be a 3 mm×3 mm square. The fiducial marker 134 may be made of a thin material. Suitable materials include, but are not limited to, any materials that will not obstruct the transducer from obtaining an ultrasound scan of the target 136. The fiducial marker 134 may be adhered to the skin surface 137 of a target 136 using any suitable methods and/or any suitable adhesives. In another aspect, the fiducial marker 134 may be stamped, inked or otherwise applied to the skin surface using ink or any other suitable, visually identifiable marking material(s).

Figure 2:
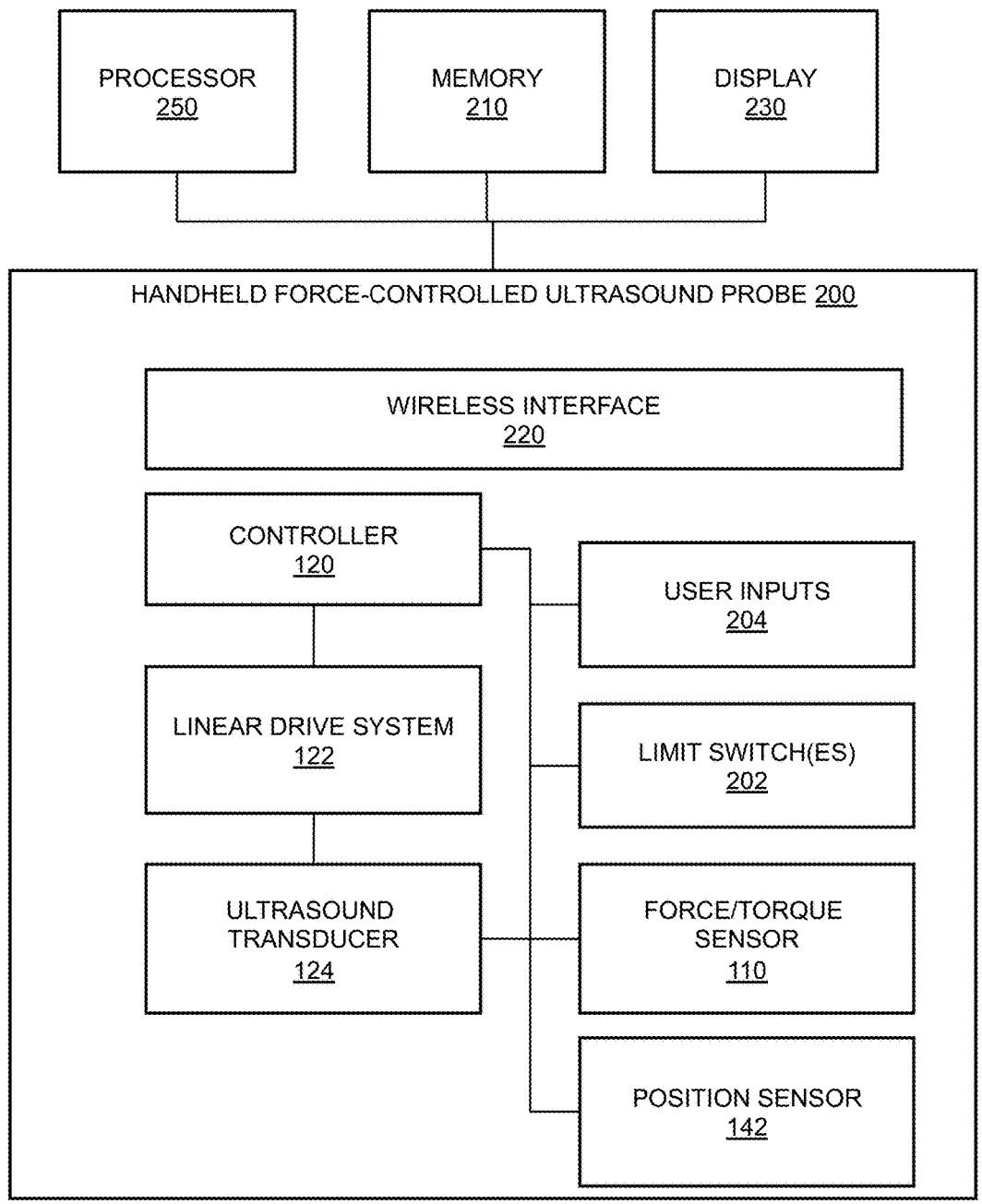
FIG. 2 is a schematic view of a handheld ultrasound probe.

FIG. 2 is a schematic depiction of a handheld force-controlled ultrasound probe. The probe 200, which may be a force-controlled ultrasound probe, generally includes a sensor 110, a controller 120, a linear drive system 122, position sensor 142, and an ultrasound transducer 124 as described above.

In contrast to the probe 112 mounted in the device 100 as described in FIG. 1, the probe 200 of FIG. 2 may have the sensor 110, controller 120, and linear drive system 122 integrally mounted (as opposed to mounted in a separate device 100) in a single device to provide a probe 200 with an integral structure. In FIG. 2, the components are all operable to gather ultrasound images at measured and/or controlled forces and torques, as described above with reference to FIG. 1. More generally, the various functions of the above-described components may be distributed across several independent devices in various ways (e.g., an ultrasound probe with integrated force/torque sensors but external drive system, an ultrasound probe with an internal drive system but external control system, etc.). In one aspect, a wireless handheld probe 200 may be provided that transmits sensor data and/or ultrasound data wirelessly to a remote computer that captures data for subsequent analysis and display. All such permutations are within the scope of this disclosure.

The ultrasound transducer 124 can include a medical ultrasonic transducer, an industrial ultrasonic transducer, or the like. Like the ultrasound probe 112 described above with reference to FIG. 1, it will be appreciated that a variety of embodiments of the ultrasound transducer 124 are possible, including embodiments directed to non-medical applications such as nondestructive ultrasonic testing of materials and objects and the like, or more generally, transducers or other transceivers or sensors for capturing data instead of or in addition to ultrasound data. Thus, although reference is made to an "ultrasound probe" in this document, the techniques described herein are more generally applicable to any context in which the transmission of energy (e.g., sonic energy, electromagnetic energy, thermal energy, etc.) from or through a target varies as a function of the contact force between the energy transmitter and the target.

Other inputs/sensors may be usefully included in the probe 200. For example, the probe 200 may include a limit switch 202 or multiple limit switches 202. These may be positioned at any suitable location(s) to detect limits of travel of the linear drive system 122, and may be used to prevent damage or other malfunction of the linear drive system 122 or other system components. The limit switch(es) may be electronically coupled to the controller 120 and provide a signal to the controller 120 to indicate when the limit switch 202 detects an end of travel of the linear drive system along the actuation axis. The limit switch 202 may include any suitable electro-mechanical sensor or combination of sensors such as a contact switch, proximity sensor, range sensor, magnetic coupling, and so forth.

The position sensor 142 may be electronically and/or mechanically coupled to the limit switch(es) 202 to provide positioning information to the controller 120 concerning physical limits marked by the limit switch(es) 202. The position sensor 142 may provide position information to the controller 120 by tracking the travel of the probe 200 along the actuation axis 114 relative to the limit switch(es) 202. The controller 120 may receive the position information from the position sensor 142, determine the position of the probe 200, e.g., relative to the limit switch positions, and may provide control signals to movement of the probe 200 too close to the limit(s) of travel defined by the limit switch(es) 202.

The probe 200 may also or instead include one or more user inputs 204. These may be physically realized by buttons, switches, dials, or the like on the probe 200. The user inputs 204 may be usefully positioned in various locations on an exterior of the probe 200. For example, the user inputs 204 may be positioned where they are readily finger-accessible while gripping the probe 200 for a scan. In another aspect, the user inputs 204 may be positioned away from usual finger locations so that they are not accidentally activated while manipulating the probe 200 during a scan. The user inputs 204 may generally be electronically coupled to the controller 120, and may support or activate functions such as initiation of a scan, termination of a scan, selection of a current contact force as the target contact force, storage of a current contact force in memory for subsequent recall, or recall of a predetermined contact force from memory. Thus, a variety of functions may be usefully controlled by a user with the user inputs 204.

A memory 210 may be provided to store ultrasound data from the ultrasound transducer and/or sensor data acquired from any of the sensors during an ultrasound scan. The memory 210 may be integrally built into the probe 200 to operate as a standalone device, or the memory 210 may include remote storage, such as in a desktop computer, network-attached storage, or other device with suitable storage capacity. In one aspect, data may be wirelessly transmitted from the probe 200 to the memory 210 to permit wireless operation of the probe 200. The probe 200 may include any suitable wireless interface 220 to accommodate such wireless operation, such as for wireless communications with a remote storage device (which may include the memory 210). The probe 200 may also or instead include a wired communications interface for serial, parallel, or networked communication with external components.

A display 230 may be provided, which may receive wired or wireless data from the probe 200. The display 230 and memory 210 may be a display and memory of a desktop computer or the like, or may be standalone accessories to the probe 200, or may be integrated into a medical imaging device that includes the probe 200, memory 210, display 230 and any other suitable hardware, processor(s), and the like. The display 230 may display ultrasound images obtained from the probe 200 using known techniques. The display 230 may also or instead display a current contact force or instantaneous contact force measured by the sensor 110, which may be superimposed on a corresponding ultrasound image or in another display region of the display 230. Other useful information, such as a target contact force, an actuator displacement, or an operating mode, may also or instead be usefully rendered on the display 230 to assist a user in obtaining ultrasound images.

A processor 250 may also be provided. In one aspect, the processor 250, memory 210, and display 230 are a desktop or laptop computer. In another aspect, these components may be separate, or some combination of these. For example, the display 230 may be a supplemental display provided for use by a doctor or technician during an ultrasound scan. The memory 210 may be a network-attached storage device or the like that logs ultrasound images and other acquisition state data. The processor 250 may be a local or remote computer provided for post-scan or in-scan processing of data. In general, the processor 250 and/or a related computing device may have sufficient processing capability to perform the quantitative processing described below. For example, the processor 250 may be configured to process an image of a subject from the ultrasound transducer 124 of the probe 200 to provide an estimated image of the subject at a predetermined contact force of the ultrasound transducer. This may, for example, be an estimate of the image at zero Newtons (no applied force), or an estimate of the image at some positive value (e.g., one Newton) selected to normalize a plurality of images from the ultrasound transducer 124. Details of this image processing are provided below by way of example with reference to FIG. 6.

Figure 3:
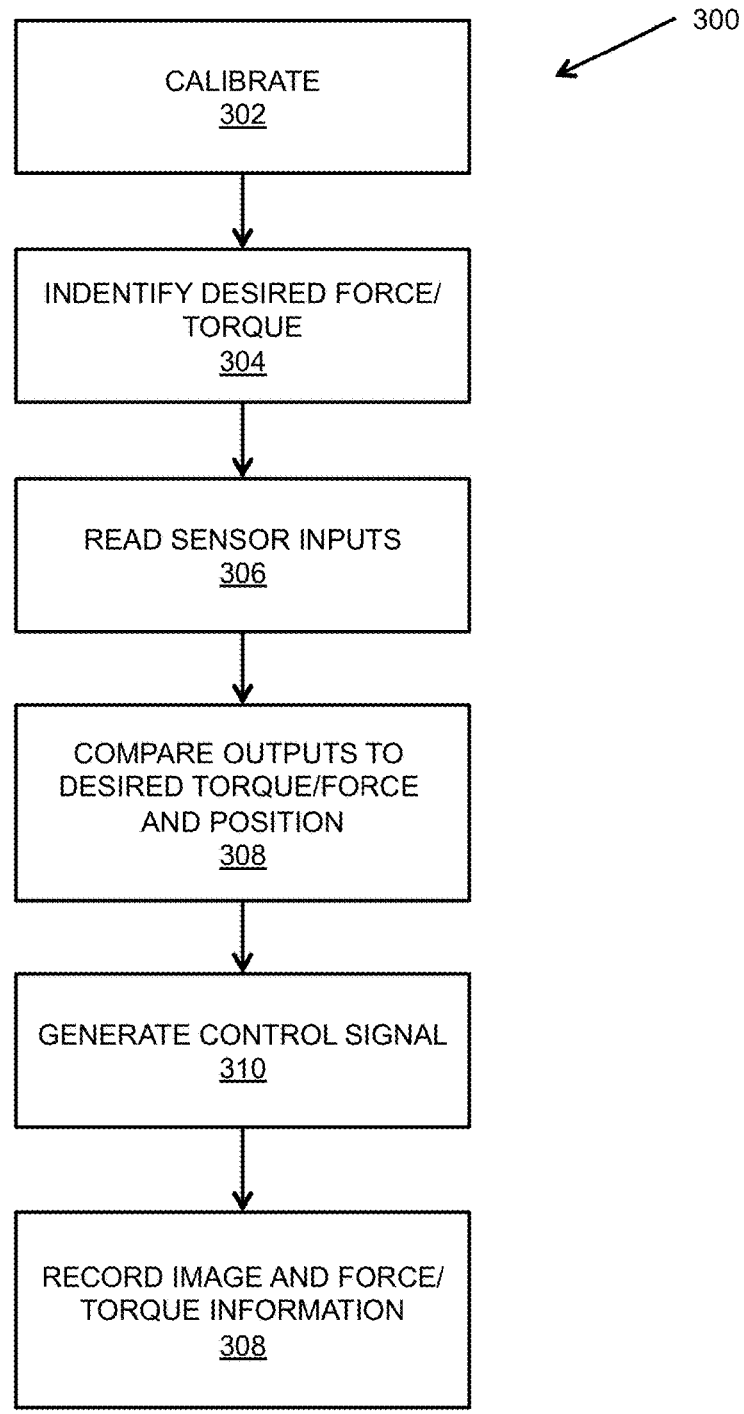
FIG. 3 is a flowchart of a process for force-controlled acquisition of ultrasound images.

FIG. 3 is a flowchart of a process for force-controlled acquisition of ultrasound images. The process 300 can be performed, e.g., using a handheld ultrasound probe 112 mounted in a device 100, or a handheld ultrasound probe 200 with integrated force control hardware.

As shown in step 302, the process 300 may begin by calibrating the force and/or torque sensors. The calibration step is for minimizing (or ideally, eliminating) errors associated with the weight of the ultrasound probe or the angle at which the sensors are mounted with respect to the ultrasound transducer, and may be performed using a variety of calibration techniques known in the art.

To compensate for the mounting angle, the angle between the sensor axis and the actuation axis may be independently measured (e.g., when the sensor is installed). This angle may be subsequently stored for use by the controller to combine the measured forces and/or torques along each axis into a single vector, using standard coordinate geometry. (E.g., for a mounting angle θ, scaling the appropriate measured forces by sin(θ) and cos(θ) prior to combining them.)

To compensate for the weight of the ultrasound probe, a baseline measurement may be taken, during a time at which the ultrasound probe is not in contact with the target. Any measured force may be modeled as due either to the weight of the ultrasound probe, or bias inherent in the sensors. In either case, the baseline measured force may be recorded, and may be subtracted from any subsequent force measurements. Where data concerning orientation of the probe is available, this compensation may also be scaled according to how much the weight is contributing to a contact force normal to the contact surface. Thus for example an image from a side (with the probe horizontal) may have no contribution to contact force from the weight of the probe, while an image from a top (with the probe vertical) may have the entire weight of the probe contributing to a normal contact force. This variable contribution may be estimated and used to adjust instantaneous contact force measurements obtained from the probe.

As shown in step 304, a predetermined desired force may be identified. In some implementations, the desired force is simply a constant force. For example, in imaging a human patient, a constant force of less than or equal 20 Newtons is often desirable for the comfort and safety of the patient.

In some implementations, the desired force may vary as a function of time. For example, it is often useful to "poke" a target in a controlled manner, and acquire images of the target as it deforms during or after the poke. The desired force may also or instead include a desired limit (minimum or maximum) to manually applied force. In some implementations, the desired force may involve a gradual increase of force given by a function $F(t)$ to a force $F_{max}$ at a time $t_{max}$, and then a symmetric reduction of force until the force reaches zero. Such a function is often referred to as a "generalized tent map," and may be given by the function $G(t)=F(t)$ if $t<t_{max}$, and $G(t)=F_{max}-F(t-t_{max})$ for $t \geq t_{max}$. When F is a linear function, the graph of $G(t)$ resembles a tent, hence the name. In another aspect, a desired force function may involve increasing the applied force by some function $F(t)$ for a specified time period until satisfactory imaging (or patient comfort) is achieved, and maintaining that force thereafter until completion of a scan. The above functions are given by way of example. In general, any predetermined force function can be used.

As shown in step 306, the output from the force and/or torque and position sensors may be read as sensor inputs to a controller or the like.

As shown in step 308, these sensor inputs may be compared to the desired force function to determine a force differential. In some implementations, the comparison can be accomplished by computing an absolute measure such as the difference of the sensor output with the corresponding desired sensor output. Similarly, a relative measure such as a ratio of output to the desired output can be computed. Additionally, output from the position sensor 142 may be compared to the positions of the limit switch(es) 202 to determine if the probe 200 is approaching an end of travel of the linear drive system 122. Many other functions can be used.

As shown in step 310, a control signal may be generated based on the comparison of actual-to-desired sensor outputs (or, from the perspective of a controller/processor, sensor inputs). The control signal may be such that the linear drive system is activated in such a way as to cause the measured force and/or torque to be brought closer to a desired force and/or torque at a given time. For example, if a difference between the measured force and the desired force is computed, then the drive system can translate the probe with a force whose magnitude is proportional to the difference, and in a direction to reduce or minimize the difference. Similarly, if a ratio of the desired force and measured force is computed, then the drive system can translate the probe with a force whose magnitude is proportional to one minus this ratio.

More generally, any known techniques from control theory can be used to drive the measured force towards the desired force. These techniques include linear control algorithms, proportional-integral-derivative ("PID") control algorithms, fuzzy logic control algorithms, etc. By way of example, the control signal may be damped in a manner that avoids sharp movements of the probe against a patient's body. In another aspect, a closed-loop control system may be adapted to accommodate ordinary variations in a user's hand position. For example, a human hand typically has small positional variations with an oscillating frequency of about four Hertz to about twenty Hertz. As such, the controller may be configured to compensate for an oscillating hand movement of a user at a frequency between four Hertz and thirty Hertz or any other suitable range. Thus, the system may usefully provide a time resolution finer than twenty Hertz or thirty Hertz, accompanied by an actuation range within the time resolution larger than typical positional variations associated with jitter or tremors in an operator's hand.

As shown in step 312, the ultrasound probe can acquire an image, a fraction of an image, or more than one image. It will be understood that this may generally occur in parallel with the force control steps described above, and images may be captured at any suitable increment independent of the time step or time resolution used to provide force control. The image(s) (or fractions thereof) may be stored together with contact force and/or torque information (e.g., instantaneous contact force and torque) applicable during the image acquisition. In some implementations, the contact force and/or torque information includes all the information produced by the force and/or torque sensors, such as the moment-by-moment output of the sensors over the time period during which the image was acquired. In some implementations, other derived quantities can be computed and stored, such as the average or mean contact force and/or torque, the maximum or minimum contact force and/or torque, and so forth.

It will be understood that the steps of the above methods may be varied in sequence, repeated, modified, or deleted, or additional steps may be added, all without departing from the scope of this disclosure. By way of example, the step of identifying a desired force may be performed a single time where a constant force is required, or continuously where a time-varying applied force is desired. Similarly, measuring contact force may include measuring instantaneous contact force or averaging a contact force over a sequence of measurements during which an ultrasound image is captured. In addition, operation of the probe in clinical settings may include various modes of operation each having different control constraints. Some of these modes are described below with reference to FIG. 5. Thus, the details of the foregoing will be understood as non-limiting examples of the systems and methods of this disclosure.

Figure 4:
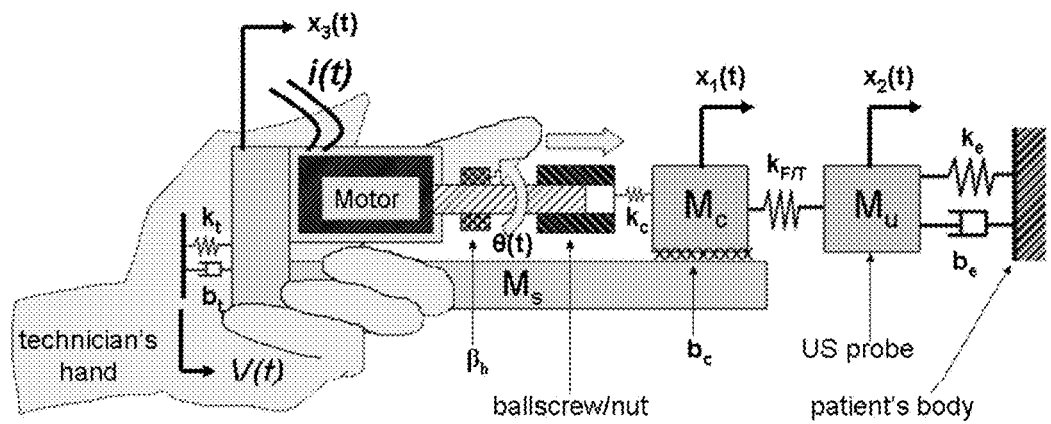
FIG. 4 shows a lumped parameter model of the mechanical system of a probe as described herein.

FIG. 4 shows a lumped parameter model of the mechanical system of a probe as described herein. While a detailed mathematical derivation is not provided, and the lumped model necessarily abstracts away some characteristics of an ultrasound probe, the model of FIG. 4 provides a useful analytical framework for creating a control system that can be realized using the controller and other components described above to achieve force-controlled acquisition of ultrasound images.

In general, the model 400 characterizes a number of lumped parameters of a controlled-force probe. The physical parameters for an exemplary embodiment are as follows. $M_u$ is the mass of ultrasound probe and mounting hardware, which may be 147 grams. $M_c$ is the mass of a frame that secures the probe, which may be 150 grams. $M_s$ is the mass of the linear drive system, which may be 335 grams. $k_{F/T}$ is the linear stiffness of a force sensor, which may be $1.1*10^5$ N/m. $k_e$ is the target skin stiffness, which may be 845 N/m. $b_e$ is the viscous damping coefficient of the target, which may be 1500 Ns/m. $k_t$ is the user's total limb stiffness, which may be 1000 N/m. $b_t$ is the user's total limb viscous damping coefficient, which may be 5000 Ns/m. $b_c$ is the frame viscous damping coefficient, which may be 0 Ns/m. $k_c$ is the stiffness of the linear drive system, which may be $3*10^7$ for an exemplary ballscrew and nut drive. $K_T$ is the motor torque constant, which may be 0.0243 Nm/A. $\beta_b$ is be the linear drive system viscous damping, which may be $2*10^{-4}$ for an exemplary ballscrew and motor rotor. L is the linear drive system lead, which may be $3*10^{-4}$ for an exemplary ballscrew. $J_{tot}$ is the moment of inertia, which may be $1.24*10^{-6}$ kgm$^2$ for an exemplary ballscrew and motor rotor.

Using these values, the mechanical system can be mathematically modeled, and a suitable control relationship for implementation on the controller can be determined that permits application of a controlled force to the target surface by the probe. Stated differently, the model may be employed to relate displacement of the linear drive system to applied force in a manner that permits control of the linear drive system to achieve an application of a controlled force to the target surface. It will be readily appreciated that the lumped model described above is provided by way of illustration and not limitation. Variations may be made to the lumped model and the individual parameters of the model, either for the probe described above or for probes having different configurations and characteristics, and any such model may be usefully employed provided it yields a control model suitable for implementation on a controller as described above.

Figure 5:
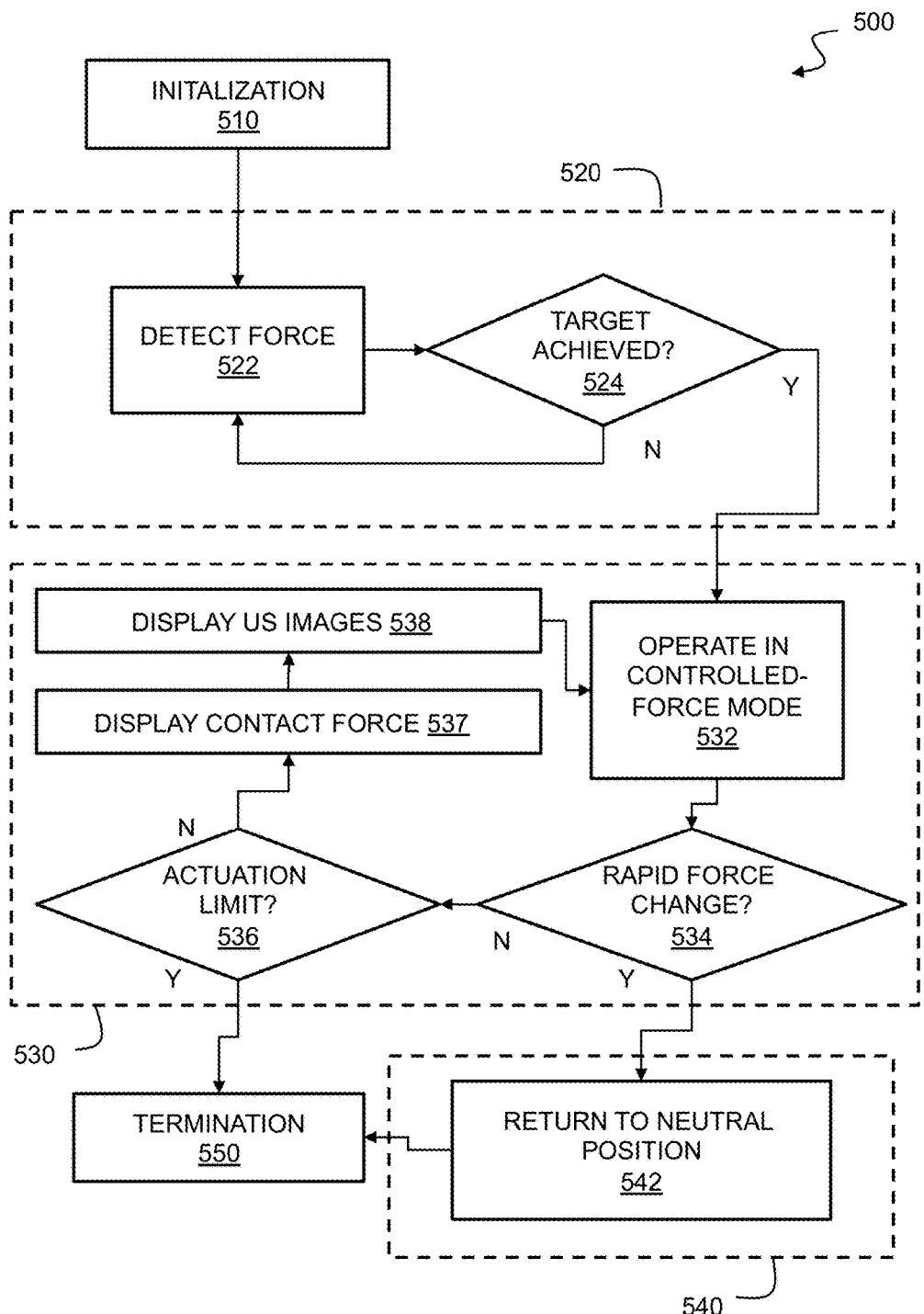
FIG. 5 is a flowchart depicting operating modes of a force-controlled ultrasound probe.

FIG. 5 is a flowchart depicting operating modes of a force-controlled ultrasound probe. While the probe described above may be usefully operated in a controlled-force mode as discussed above, use of the handheld probe in clinical settings may benefit from a variety of additional operating modes for varying circumstances such as initial contact with a target surface or termination of a scan. Several useful modes are now described in greater detail.

In general, the process 500 includes an initialization mode 510, a scan initiation mode 520, a controlled-force mode 530, and a scan termination mode 540, ending in termination 550 of the process 500.

As shown in step 510, an initialization may be performed on a probe. This may include, for example, powering on various components of the probe, establishing a connection with remote components such as a display, a memory, and the like, performing any suitable diagnostic checks on components of the probe, and moving a linear drive system to a neutral or ready position, which may for example be at a mid-point of a range of movement along an actuation axis.

As shown in step 522, the scan initiation mode 520 may begin by detecting a force against the probe using a sensor, such as any of the sensors described above. In general, prior to contact with a target surface such as a patient, the sensed force may be at or near zero. In this state, it would be undesirable for the linear drive system to move to a limit of actuation in an effort to achieve a target controlled force. As such, the linear drive system may remain inactive and in a neutral or ready position during this step.

As shown in step 524, the controller may check to determine whether the force detected in step 522 is at or near a predetermined contact force such as the target contact force for a scan. If the detected force is not yet at (or sufficiently close to) the target contact force, then the initiation mode 520 may return to step 522 where an additional force measurement is acquired. If the force detected in step 522 is at or near the predetermined contact force, the process 500 may proceed to the controlled-force mode 530. Thus, a controller disclosed herein may provide an initiation mode in which a linear drive system is placed in a neutral position and a force sensor is measured to monitor an instantaneous contact force, the controller transitioning to controlled-force operation when the instantaneous contact force meets a predetermined threshold. The predetermined threshold may be the predetermined contact force that serves as the target contact force for controlled-force operation, or the predetermined threshold may be some other limit such as a value sufficiently close to the target contact force so that the target contact force can likely be readily achieved through actuation of the linear drive system. The predetermined threshold may also or instead be predictively determined, such as by measuring a change in the measured contact force and extrapolating (linearly or otherwise) to estimate when the instantaneous contact force will equal the target contact force.

As shown in step 532, the controlled-force mode 530 may begin by initiating controlled-force operation, during which a control system may be executed in the controller to maintain a desired contact force between the probe and a target, all as generally discussed above.

While in the controlled-force mode 530, other operations may be periodically performed. For example, as shown in step 534, the current contact force may be monitored for rapid changes. In general, a rapid decrease in contact force may be used to infer that a probe operator has terminated a scan by withdrawing the probe from contact with a target surface. This may be for example, a step decrease in measured force to zero, or any other pattern of measured force that deviates significantly from expected values during an ongoing ultrasound scan. If there is a rapid change in force, then the process 500 may proceed to the termination mode 540. It will be appreciated that this transition may be terminated where the force quickly returns to expected values, and the process may continue in the controlled-force mode 530 even where there are substantial momentary variations in measure force. As shown in step 536, limit detectors for a linear drive system may be periodically (or continuously) monitored to determine whether an actuation limit of the linear drive system has been reached. If no such limit has been reached, the process 500 may continue in the controlled-force mode 530 by proceeding for example to step 537. In one example, if an actuation limit has been reached, then the process may proceed to termination 550 where the linear drive system is disabled. In another example, if an actuation limit has been reached, an endpoint avoidance strategy may be enabled to maintain the current position and force as described in more detail in FIG. 12. It will be appreciated that the process 500 may instead proceed to the termination mode 540 to return the linear drive system to a neutral position for future scanning.

As shown in step 537, a contact force, such as a force measured with any of the force sensors described above, may be displayed in a monitor or the like. It will be appreciated that the contact force may be an instantaneous contact force or an average contact force for a series of measurements over any suitable time interval. The contact force may, for example, be displayed alongside a target contact force or other data. As shown in step 538, ultrasound images may be displayed using any known technique, which display may be alongside or superimposed with the force data and other data described above.

As shown in step 542, when a rapid force change or other implicit or explicit scan termination signal is received, the process 500 may enter a scan termination mode 540 in which the linear drive system returns to a neutral or ready position using any suitable control algorithm, such as a controlled-velocity algorithm that returns to a neutral position (such as a mid-point of an actuation range) at a constant, predetermined velocity. When the linear drive system has returned to the ready position, the process 500 may proceed to termination as shown in step 550, where operation of the linear drive system is disabled or otherwise terminated.

Thus, it will be appreciated that a method or system disclosed herein may include operation in at least three distinct modes to accommodate intuitive user operation during initiation of a scan, controlled-force scanning, and controlled-velocity exit from a scanning mode. Variations to each mode will be readily envisioned by one of ordinary skill in the art and are intended to fall within the scope of this disclosure. Thus, for example any one of the modes may be entered or exited by explicit user input. In addition, the method may accommodate various modes of operation using the sensors and other hardware described above. For example the controlled-force mode 530 may provide for user selection or input of a target force for controlled operation using, e.g., any of the user inputs described above.

More generally, the steps described above may be modified, reordered, or supplemented in a variety of ways. By way of example, the controlled-force mode of operation may include a controlled-velocity component that limits a rate of change in position of the linear drive system. Similarly, the controlled-velocity mode for scan termination may include a controlled-force component that checks for possible recovery of controlled-force operation while returning the linear drive system to a neutral position. All such variations, and any other variations that would be apparent to one of ordinary skill in the art, are intended to fall within the scope of this disclosure.

In general, the systems described above facilitate ultrasound scanning with a controlled and repeatable contact force. The system may also provides a real time measurement of the applied force when each ultrasound image is captured, thus permitting a variety of quantitative analysis and processing steps that can normalize images, estimate tissue elasticity, provide feedback to recover a previous scan state, and so forth. Some of these techniques are now described below in greater detail.

Figure 6:
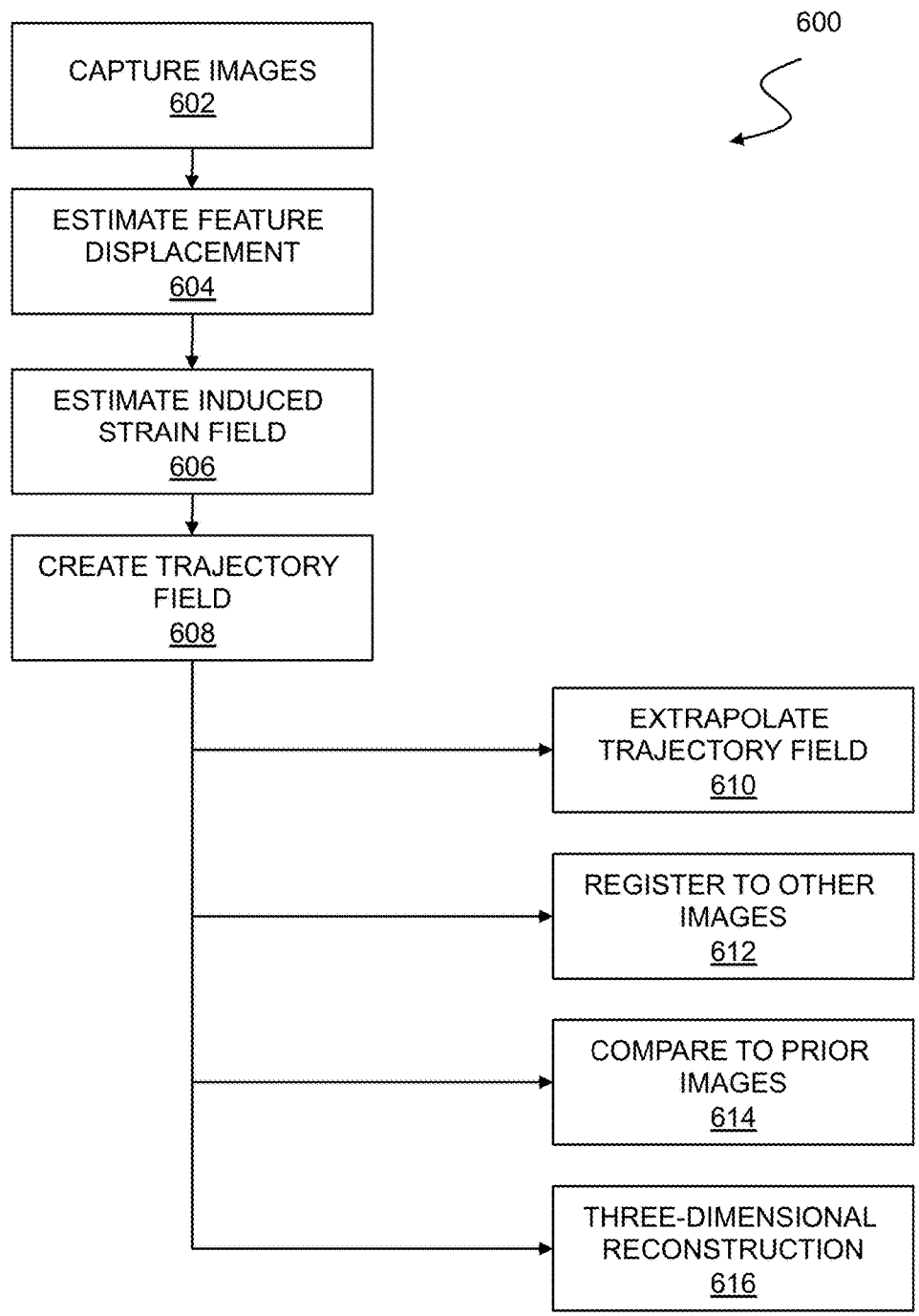
FIG. 6 shows a process for ultrasound image processing.

FIG. 6 shows a process 600 for ultrasound image processing.

As shown in step 602, the process may begin with capturing a plurality of ultrasound images of an object such as human tissue. In general, each ultrasound image may contain radio frequency echo data from the object, and may be accompanied by a contact force measured between an ultrasound transducer used to obtain the plurality of ultrasound images and a surface of the object. The contact force may be obtained using, e.g., any of the hand-held, controlled force ultrasound scanners described above or any other device capable of capturing a contact force during an ultrasound scan. The contact force may be manually applied, or may be dynamically controlled to remain substantially at a predetermined value. It will be appreciated that the radio frequency echo data may be, for example, A-mode or B-mode ultrasound data, or any other type of data available from an ultrasound probe and suitable for imaging. More generally, the techniques described herein may be combined with any force-dependent imaging technique (and/or contact-force-dependent imaging subject) to facilitate quantitative analysis of resulting data.

As shown in step 604, the process 600 may include estimating a displacement of one or more features between two or more of the ultrasound images to provide a displacement estimation. A variety of techniques are available for estimating pixel displacements in two-dimensional ultrasound images, such as B-mode block-matching, phase-based estimation, RF speckle tracking, incompressibility-based analysis, and optical flow. In one aspect, two-dimensional displacement estimation may be based on an iterative one-dimensional displacement estimation scheme, with lateral displacement estimation performed at locations found in a corresponding axial estimation. As described for example in U.S. Provisional Application No. 61/429,308 filed on Jan. 3, 2011 and incorporated herein by reference in its entirety, coarse-to-fine template-matching may be performed axially, with normalized correlation coefficients used as a similarity measure Subsample estimation accuracy may be achieved with curve fitting. Regardless of how estimated, this step generally results in a two-dimensional characterization (e.g., at a feature or pixel level) of how an image deforms from measurement to measurement.

It will be understood that feature tracking for purposes of displacement estimation may be usefully performed on a variety of different representations of ultrasound data. Brightness mode (or "B-mode") ultrasound images provide a useful visual representation of a transverse plane of imaged tissue, and may be used to provide the features for which displacement in response to a known contact force is tracked. Similarly, an elastography images (such as stiffness or strain images) characterize such changes well, and may provide two-dimensional images for feature tracking.

As shown in step 606, the process 600 may include estimating an induced strain field from the displacement. In general, hyperelastic models for mechanical behavior work well with subject matter such as human tissue that exhibits significant nonlinear compression. A variety of such models are known for characterizing induced strain fields. One such model that has been usefully employed with tissue phantoms is a second-order polynomial model described by the strain energy function:

$$U = \sum_{i+j=1}^{2} C_{ij}(I_1 - 3)^i (I_2 - 3)^j + \sum_{i=1}^{2} \frac{1}{D_i}(J_{el} - 1)^{2i} \qquad [\text{Eq. 1}]$$

where U is the strain energy per unit volume, $I_1$ and $I_2$ are the first and second deviatoric strain invariant, respectively, and $J_{el}$ is the elastic volume strain. The variables $C_{ij}$ are the material parameters with the units of force per unit area, and the variables $D_i$ are compressibility coefficients that are set to zero for incompressible materials. Other models are known in the art, and may be usefully adapted to estimation of a strain field for target tissue as contemplated herein.

As shown in step 608, the process 600 may include creating a trajectory field that characterizes a displacement of the one or more features according to variations in the contact force. This may include characterizing the relationship between displacement and contact force for the observed data using least-square curve fitting with polynomial curves of the form:

$$x_{i,j}(f) = \Sigma_{k=0}^{N} \alpha_{i,j,k} f^k \quad \text{[Eq. 2]}$$

$$y_{i,j}(f) = \Sigma_{k=0}^{N} \beta_{i,j,k} f^k \quad \text{[Eq. 3]}$$

where $x_{i,j}$ and $y_{i,j}$ are the lateral and axial coordinates, respectively of a pixel located at the position (i,j) of a reference image, and $\alpha$ and $\beta$ are the parameter sets determined in a curve fitting procedure. The contact force is f, and N denotes the order of the polynomial curves. Other error-minimization techniques and the like are known for characterizing such relationships, many of which may be suitably adapted to the creation of a trajectory field as contemplated herein.

With a trajectory field established for a subject, a variety of useful real-time or post-processing steps may be performed, including without limitation image correction or normalization, analysis of tissue changes over time, registration to data from other imaging modalities, feedback and guidance to an operator/technician (e.g., to help obtain a standard image), and three-dimensional image reconstruction. Without limiting the range of post-processing techniques that might be usefully employed, several examples are now discussed in greater detail.

As shown in step 610, post-processing may include extrapolating the trajectory field to estimate a location of the one or more features at a predetermined contact force, such as to obtain a corrected image. The predetermined contact force may, for example, be an absence of applied force (i.e., zero Newtons), or some standardized force selected for normalization of multiple images (e.g., one Newton), or any other contact force for which a corrected image is desired, either for comparison to other images or examination of deformation behavior. With the relationship between contact force and displacement provided from step 608, location-by-location (e.g., feature-by-feature or pixel-by-pixel) displacement may be determined for an arbitrary contact force using Eqs. 2 and 3 above, although it will be appreciated that the useful range for accurate predictions may be affected by the range of contact forces under which actual observations were made.

As shown in step 612, post-processing may include registering an undistorted image to an image of an object obtained using a different imaging modality. Thus ultrasound results may be registered to images from, e.g., x-ray imaging, x-ray computed tomography, magnetic resonance imaging ("MRI"), optical coherence tomography, positron emission tomography, and so forth. In this manner, elastography data that characterizes compressibility of tissue may be registered to other medical information such as images of bone and other tissue structures.

As shown in step 614, post-processing may include comparing an undistorted image to a previous undistorted image of an object. This may be useful, for example, to identify changes in tissue shape, size, elasticity, and composition over a period of time between image captures. By normalizing a contact force or otherwise generating corrected or undistorted images, a direct comparison can be made from one undistorted image to another undistorted image captured weeks, months, or years later.

As shown in step 616, post-processing may also or instead include capturing multiple undistorted images of a number of transverse planes of an object such as human tissue. Where these images are normalized to a common contact force, they may be registered or otherwise combined with one another to obtain a three-dimensional image of the object. The resulting three-dimensional image(s) may be further processed, either manually or automatically (or some combination of these), for spatial analysis such as measuring a volume of a specific tissue within the object, or measuring a shape of the tissue.

Still more generally, any post-processing for improved imaging, diagnosis, or other analysis may be usefully performed based on the quantitative characterizations of elastography described above. For example, an ultrasound image of an artery may be obtained, and by measuring an amount of compression in the artery in response to varying contact forces, blood pressure may be estimated. Similarly, by permitting reliable comparisons of time-spaced data, better diagnosis/detection of cancerous tissue can be achieved. Any such ultrasound imaging applications that can be improved with normalized data can benefit from the inventive concepts disclosed herein.

Figure 7:
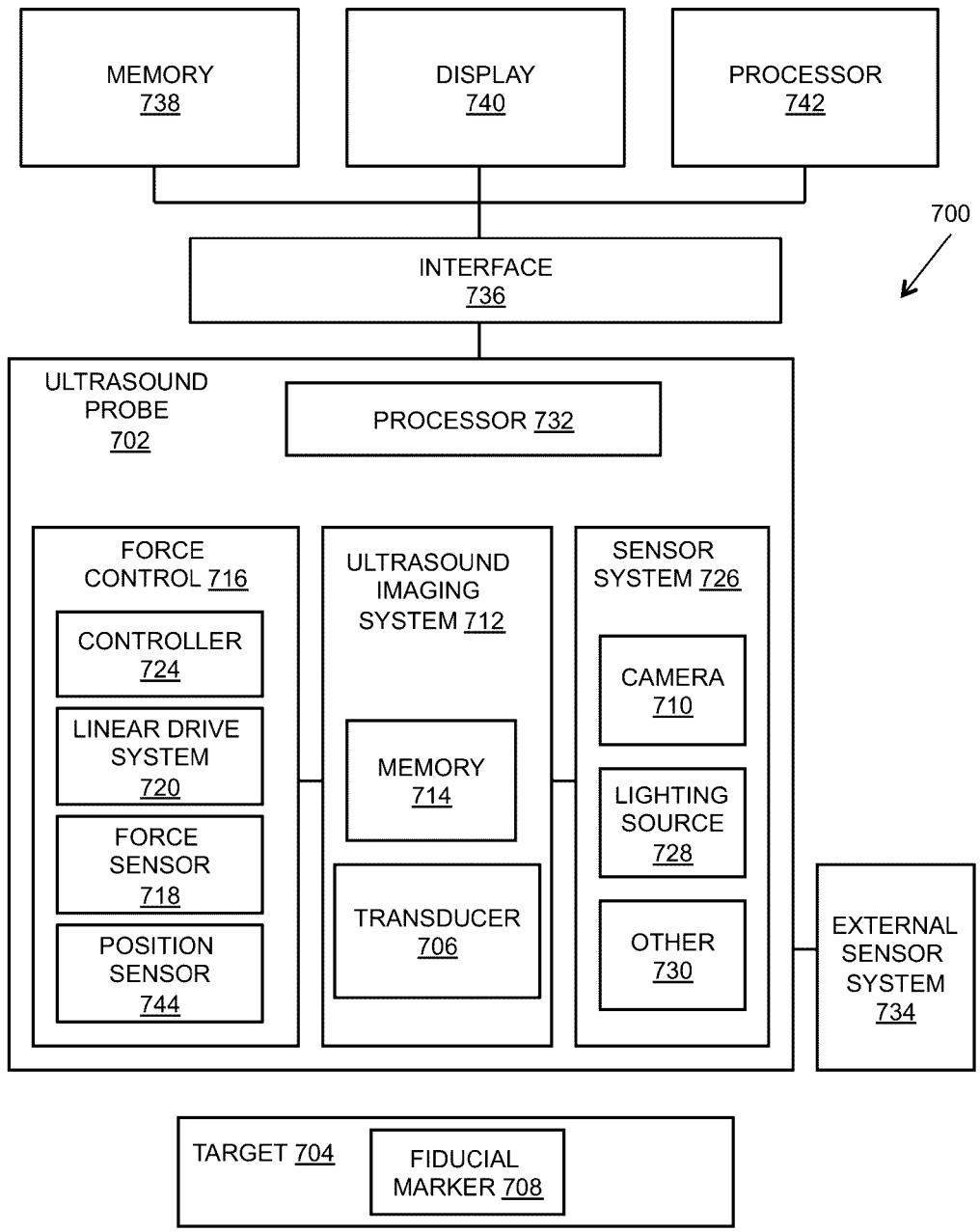
FIG. 7 is a schematic view of an ultrasound scanning system.

FIG. 7 is a schematic view of an ultrasound scanning system 700. The system 700 may be used to capture an acquisition state for a handheld ultrasound probe 702, such as any of the devices described above, including quantitative data about the conditions under which the scan was obtained. The conditions may include, e.g., a contact force of the handheld ultrasound probe 702, a pose of the ultrasound probe 702 in relation to a target 704, and/or any other data that might be useful in interpreting or further processing image data. In one aspect, data on the contact force and/or pose may be used to obtain a three dimensional reconstructed volume of a target.

The system 700 generally includes the handheld ultrasound probe 702 to capture one or more ultrasound images of a target 704 through a skin surface in a scan, a fiducial marker 708 applied to the skin surface of the target 704, and a camera 710. While a single fiducial marker 708 is depicted, it will be understood that any number of fiducial markers, which may have identical or different features, may be used.

The ultrasound probe 702 may include an ultrasound imaging system 712 that includes the at least one transducer 706 and a memory 714. The memory 714 may be provided to store ultrasound data from the ultrasound transducer 706 and/or sensor data acquired from any of the sensors during an ultrasound scan. The ultrasound probe 702 may also include a force control system 716.

The force system control may include a force sensor 718, a linear drive system 720, an input 722, and a controller 724, as described above. The force sensor 718 may include a pressure transducer or the like configured to obtain a pressure applied by the handheld ultrasound probe 702 to the skin surface. The linear drive system 720 may be mechanically coupled to the handheld ultrasound transducer 706. The linear drive system 720 may include a control input 722 or be electronically coupled to the control input 722. The linear drive system 720 may be responsive to a control signal received at the control input 722 to translate the ultrasound transducer 706 along an actuation axis 114 as shown in FIG. 1. The linear drive system 720 may also include a position sensor 744 that may provide positioning signals to the controller 724. The controller 724 may be electronically coupled to the force sensor 718 and a control input of the linear drive system 720. The controller 724 may include processing circuitry configured to generate the control signal to the control input 722 in a manner that maintains a substantially constant predetermined contact force between the ultrasound transducer 706 and the target 704, or a contact force that varies in a predetermined manner, all as discussed above.

The ultrasound probe 702 may also include a sensor system 726 configured to obtain a pose of the ultrasound probe 702. The sensor system 726 may include the camera 710 and a lighting source 728, e.g., to capture image of the fiducial marker 708 and or other visible features to obtain camera motion data. In another aspect, the sensor system 720 may include other sensors 730 such as one or more inertial sensors, range finding sensors (such as sonic, ultrasonic, or infrared range finding subsystems), or any other circuitry or combination of circuitry suitable for tracking relative positions of the ultrasound probe 702 and/or the target 704.

The system 700 may also include a processor 732 in communication with the handheld ultrasound probe 702 and/or sub-systems thereof, either individually or through a common interface 736 such as a wired or wireless interface for the ultrasound probe 702. It will be appreciated that a wide range of architectures are possible for control and data acquisition for the system 700, including for example, a processor on the ultrasound probe, a processor remote from the ultrasound probe coupled directly to one or more subsystems of the ultrasound probe, and various combinations of these. As such, the logical depiction of systems in FIG. 7 should be understood as illustrative only, and any arrangement of components and/or allocation of processing suitable for an ultrasound imaging system as contemplated herein may be used without departing from the scope of this disclosure. By way of non-limiting example, the processor 732 on the ultrasound probe 702 may be a controller or the like that provides a programming interface for the force control system 716, ultrasound imaging system 712, and/or sensor system 726, with system control provided by a remote processor (such as the process 742) through the interface 736. In another aspect, the processor 732 on the ultrasound probe 702 may be a microprocessor programmed to control all aspects of the ultrasound probe 702 directly, with the remote processor 742 providing only supervisory control such as initiating a scan or managing/displaying received scan data.

The processor 732 may be programmed to identify one or more predetermined features (such as the fiducial marker 708 and/or other features on the skin surface of the target 704) and calculate a pose of the handheld ultrasound probe 702 using the one or more predetermined features in an image from the camera 710. In this manner, a number of camera images, each associated with one of a number of ultrasound images, may be used to align the number of ultrasound images in a world coordinate system. The ultrasound images, when so aligned, may be combined to obtain a reconstructed volume of the target 704.

The system 700 may also include one or more external sensor systems 734. The external sensor systems 734 may be integral with or separate from the sensor system 726. The external sensor system 734 may include an external electromechanical system coupled to the handheld ultrasonic probe for tracking a pose of the handheld ultrasonic probe 702 through direct measurements, as an alternative to or in addition to image based camera motion data. The external sensor system 734 may also or instead include an external optical system, or any other sensors used for tracking a pose of the ultrasound probe 702.

The system 700 also may include an interface 736, such as a wireless interface, for coupling the handheld ultrasound probe 702 in a communicating relationship with a memory 738, a display 740, and a processor 742. The memory 738, the display 740, and the processor 742 may be separate components or they may be integrated into a single device such as a computer. Where a wireless interface is used, various techniques may be employed to provide a data/control channel consistent with medical security/privacy constraints, and/or to reduce or eliminate interference with and/or from other wireless devices.

The display 740 may include one or more displays or monitors for displaying one or more ultrasound images obtained from the ultrasound probe 702 and/or one or more digital images recorded by the camera 710, along with any other data related to a current or previous scan.

The memory 738 may be used to store, e.g., data from the handheld ultrasound probe 702 and the camera 710. The memory 738 may also store data from other devices of the system 700 such as the sensors. The memory 738 may store an acquisition state for an ultrasound image. The acquisition state may for example include the pose and the pressure of the ultrasound transducer 706 during scanning, or data for recovering any of the foregoing. The memory 738 may also or instead include a fixed or removable mass storage device for archiving scans and accompanying data. The memory 738 may be a remote memory storage device or the memory may be associated with a computer containing the processor 742. The interface 736 may include a wireless interface coupling the handheld ultrasound probe 702 in a communicating relationship with the remote storage device, processor, and/or display.

The system 700 may include any other hardware or software useful for the various functions described above. Also, the system 700 may be used for other applications including, for example, pathology tracking, elastography, data archiving or retrieval, imaging instructions, user guides, and so forth.

Figure 8:
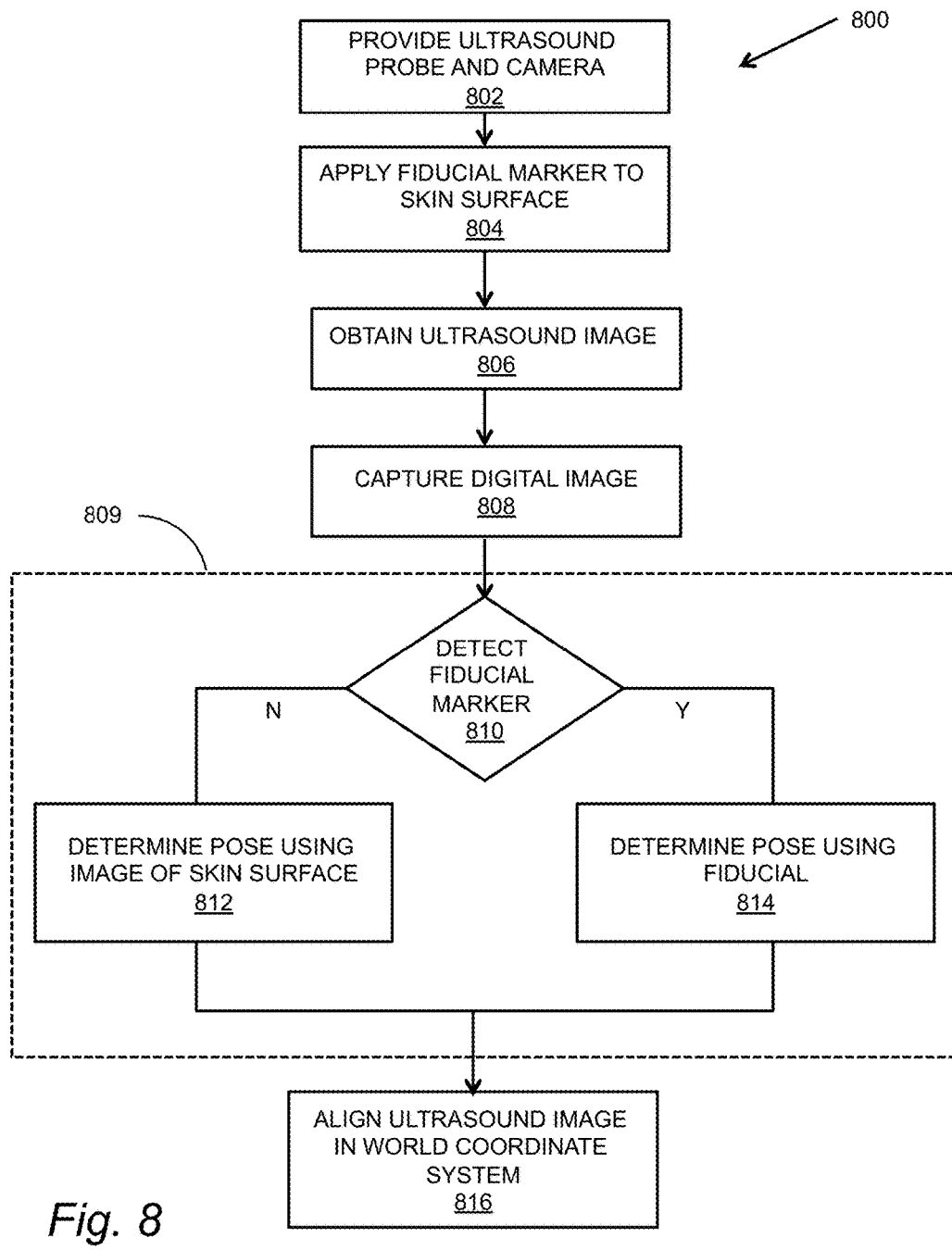
FIG. 8 is a flowchart for a process for obtaining a reconstructed volume of a target using a handheld ultrasound probe.

FIG. 8 is a flowchart for a process 800 for obtaining a reconstructed volume of a target using a handheld ultrasound probe.

As shown in step 802, a camera and ultrasound probe may be provided. The camera, which may be any of the cameras described above, may be mechanically coupled in a fixed relationship to the handheld ultrasound probe in an orientation such that the camera is positioned to capture a digital image of a skin surface of a target when the handheld ultrasound probe is placed for use against the skin surface. A lighting source may also be mechanically coupled to the ultrasound probe and positioned to illuminate the skin surface, and more particularly an area of the skin surface where the digital image is captured, when the handheld ultrasound probe is placed for use against the skin surface.

As shown in step 804, a fiducial marker with predetermined features such as predetermined dimensions may be applied to the skin surface of a target. The fiducial marker may be placed in any suitable location. In one embodiment, the fiducial marker is preferably positioned at or near the location where the ultrasound probe will contact the surface so that the camera has a clear view of the fiducial marker.

As shown in step 806, an ultrasound image of the skin surface may be obtained from the handheld ultrasound probe. This may include data on contact force, or any other data available from the ultrasound system and useful in subsequent processing.

As shown in step 808, the camera may capture a digital image of the target, or the skin surface of the target. The digital image may include features of the skin surface and/or the fiducial marker where the fiducial marker is within a field of view of the camera. The steps of obtaining an ultrasound image from the handheld ultrasound probe and obtaining a digital image from the camera may be usefully performed substantially simultaneously so that the digital image is temporally correlated to the ultrasound image. In general, the ultrasound probe may capture one or more ultrasound images and the camera may capture one or more digital images in order to provide a sequence of images forming a scan. At least one of the digital images may include the fiducial marker.

Although not depicted, a variety of supporting steps may also or instead be performed as generally described above. The method may include wirelessly transmitting ultrasound data from the handheld ultrasound probe to a remote storage facility. The method may include displaying at least one ultrasound image obtained from the handheld ultrasound probe and/or displaying at least one digital image recorded by the camera. The images may be displayed on one or more monitors, and may be displayed during a scan and/or after a scan. In one aspect, where a sequence of images is obtained, a time stamp or other sequential and/or chronological indicator may be associated with each image (or image pair, including the digital image from the camera and the ultrasound image from the probe). In this manner, a sequence of images may be replayed or otherwise processed in a manner dependent on sequencing/timing of individual images.

As shown in step 809, a camera pose may be determined. By way of example and not limitation, this may be accomplished using motion estimation, which may be further based on a fiducial marker placed upon the skin surface of a target. While the emphasis in the following description is on motion estimation using a fiducial, it will be understood that numerous techniques may be employed to estimate or measure a camera pose, and any such techniques may be adapted to use with the systems and methods contemplated herein provided they can recover motion with suitable speed and accuracy for the further processing described. Several examples are noted above, and suitable techniques may include, e.g., mechanical instrumentation of the ultrasound probe, or image-based or other external tracking of the probe.

As shown in step 810, a digital image may be analyzed to detect a presence of a fiducial marker. Where the fiducial marker is detected, the process 800 may proceed to step 814 where motion estimation is performed and the camera pose recovered using the fiducial marker. As shown in step 812, where no fiducial marker is detected, motion estimation may be performed using any other visible features of the skin surface captured by the camera. However, determined, the camera pose may be determined and stored along with other data relating to a scan. It will be understood that the "camera pose" referred to herein may be a position and orientation of the actual digital camera, or any other pose related thereto, such as any point within, on the exterior of, or external to the ultrasound probe, provided the point can be consistently related (e.g., by translation and/or rotation) to the visual images captured by the digital camera.

Once a world coordinate system is established (which may be arbitrarily selected or related to specific elements of the ultrasound system and/or the target), a three-dimensional motion of the handheld ultrasound probe with respect to the skin surface for the digital image may be estimated and the pose may be expressed within the world coordinates. World coordinates of points on a plane, $X=[X\ Y\ 1]^T$, and the corresponding image coordinates, $x=[x\ y\ 1]^T$ may be related by a homography matrix. This relationship may be expressed as:

$$[xy1]^T = K[r_1 r_2 r_3 | t][XYZ1]^T \quad [\text{Eq. 4}]$$

where K is the 3×3 projection matrix of the camera that incorporates the intrinsic parameters of the camera. The projection matrix may be obtained through intrinsic calibration of the camera. The rotation matrix R and the translation vector t describe the geometric relationship between the world coordinate system and the image coordinate system, and $r_1$, $r_2$, and $r_3$ are the column vectors of R.

World coordinates of points on a planar structure may be related by a 3×3 planar homography matrix. For points on a planar structure, $Z=0$ and the relationship may be expressed as:

$$[xy1]^T = K[r_1 r_2 | t][XY1]^T \quad [\text{Eq. 5}]$$

The image coordinates in different perspectives of a planar structure may also be related by a 3×3 planar homography matrix. An image-to-world homography matrix may then be used to show the relationship between the camera images (the image coordinate system) and the ultrasound images (a world coordinate system). The homography matrix may be expressed by the formula $x'=Hx$, where $x'=[x'\ y'\ 1']$ and $x=[x\ y\ 1]$, points $x'$ and $x$ are corresponding points in the two coordinate systems, and H is the homography matrix that maps point x to x'. H has eight degrees of freedom in this homogeneous representation and H can be determined by at least four corresponding points. H may be written as a 9-vector matrix, $[h_{11}, h_{12}, h_{13}, h_{21}, h_{23}, h_{31}, h_{32}, h_{33}]^T$, with n corresponding points, $x_i'$ and $x_i$ for $i=1, 2, 3, \ldots n$. This matrix may be expressed by the formula $A_h=0$, where A may be a 2n×9 matrix:

$$A = \begin{bmatrix} x_1 & y_1 & 1 & 0 & 0 & 0 & -x_1 x_1' & -y_1 x_1' & -x_1' \\ 0 & 0 & 0 & x_1 & y_1 & 1 & -x_1 y_1' & -y_1 y_1' & -y_1' \\ \vdots & \vdots & \vdots & \vdots & \vdots & \vdots & \vdots & \vdots & \vdots \\ x_n & y_n & 1 & 0 & 0 & 0 & -x_n x_n' & -y_n x_n' & -x_n' \\ 0 & 0 & 0 & x_n & y_n & 1 & -x_n y_n' & -y_n y_n' & -y_n' \end{bmatrix} \quad [\text{Eq. 6}]$$

The solution h is the unit eigenvector of the matrix ATA with the minimum eigenvalue. The homography matrix may be estimated by any suitable method including, for example, using a RANSAC (Random Sample Consensus) algorithm.

If the image to world homography matrix and the projection matrix of the camera are known, then the camera pose in the world coordinate system may be calculated for each image i, where $i=1, 2, 3, \ldots n$. Thus, column vectors $r_1$, $r_2$, and t can be calculated. Vector $r_3$ may be expressed as the formula $r_3 = r_1 \times r_2$ since R is a rotation matrix.

After the points or other features on the fiducial marker are selected, the corresponding features may be identified for each digital image where the fiducial marker is present. In general, the fiducial marker may be visible in at least one of the plurality of digital images (and not necessarily the first image), although it is also possible to recover camera pose entirely based on features other than the fiducial marker. The planar homography matrix from image i to the previous image may be calculated. The correspondences between consecutive images may be extracted using any suitable technique such as scale-invariant feature transform (SIFT).

As shown in step 816, the ultrasound image(s) may be aligned in the world coordinate system. The process 800 may also include a step of calibrating the ultrasound probe so that ultrasound images can be converted to camera coordinates and/or the world coordinate system, thus permitting the ultrasound image(s) to be registered in a common coordinate system. For each ultrasound image, image coordinates may be converted to world coordinates using the corresponding estimates of camera pose. Transformations derived from ultrasound calibration may also be used to convert the image coordinates to the world coordinates. A plurality of ultrasound images may be aligned to the world coordinate system based on the corresponding camera poses. The resulting ultrasound images may be further processed in three dimensions, for example to obtain a shape and/or volume of the target, or features and/or objects within the target from the plurality of ultrasound images that have been aligned in the world coordinate system. Thus for example, a shape or volume of tissue, a tumor, or any other object within the target may be calculated in three-dimensions based on the registered ultrasound images, particularly where each image is normalized as described above to a single contact force.

A processor in communication with the ultrasound probe and the camera may be configured to perform the above-described steps including: identifying the fiducial marker in two or more digital images from the camera; establishing a world coordinate system using the predetermined dimensions of the fiducial marker and the two or more digital images; estimating a three dimensional pose of the handheld ultrasound probe with respect to the two or more images; and aligning the plurality of ultrasound images in the world coordinate system to obtain a reconstructed volume of the target. It will be readily appreciated that the steps may be performed any number of times for any number of camera images and/or ultrasound images, and processing may be performed as new images are acquired, or in a post processing step according to the capabilities of the system or the preferences of a user.

Figure 9:
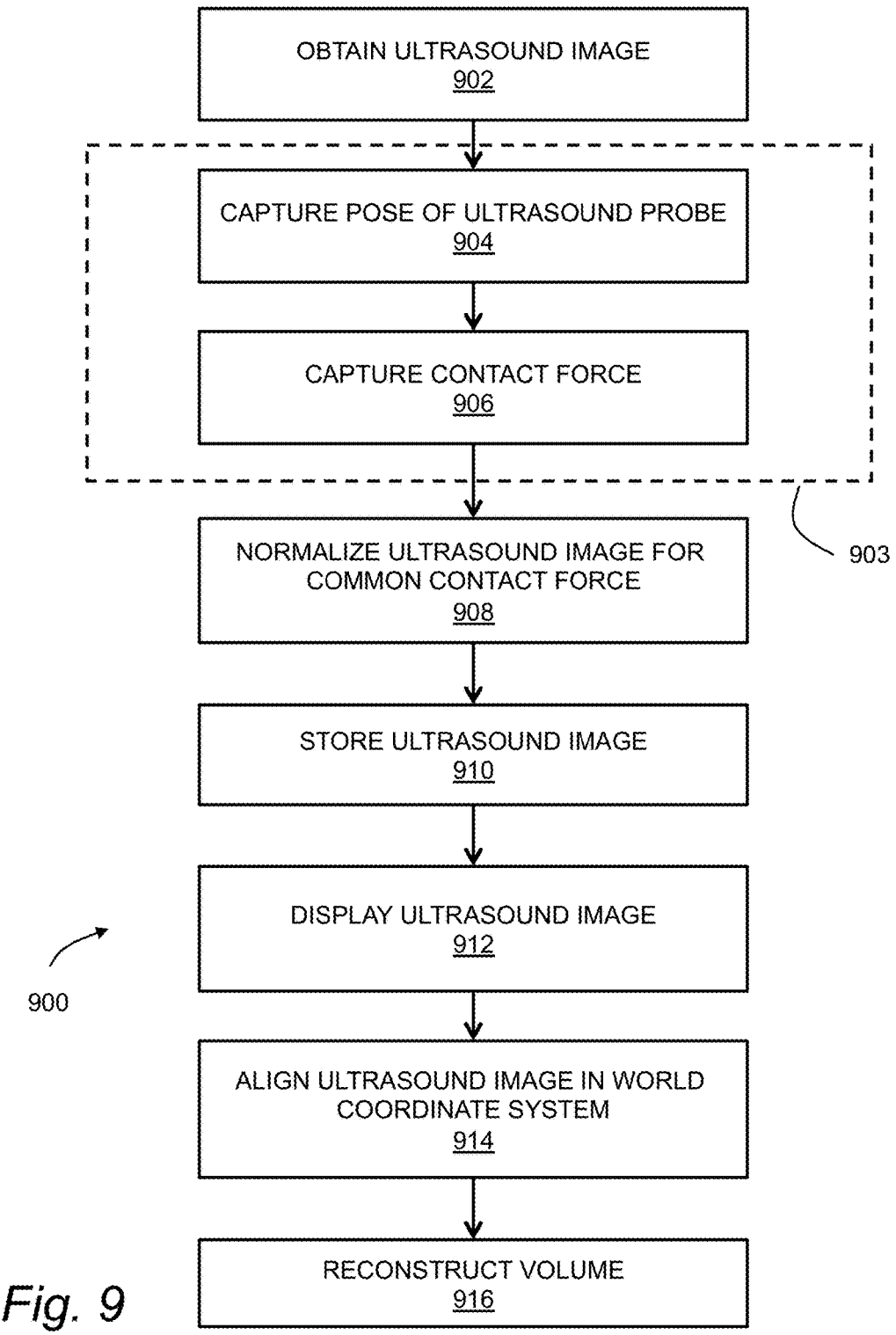
FIG. 9 is a flowchart for a process for capturing an acquisition state for an ultrasound scan.

FIG. 9 is a flowchart of a process for capturing an acquisition state for an ultrasound scan.

As shown in step 902, the process 900 may begin with capturing an ultrasound image with a handheld ultrasound probe such as any of the probes described above. The steps of the process 900 may in general performed a single time, or may be repeated any number of times according to the intended use(s) of the acquisition state data.

As depicted generally in step 903, the process 900 may include capturing acquisition state data. While various specific types of acquisition state data are described below, it will be appreciated that more generally any data related to the state of an ultrasound probe, the target, the surrounding environment, and so forth may be usefully acquired as acquisition state data and correlated to one or more ultrasound images. Thus for example, the acquisition state may include location, orientation, orientation, velocity (in any of the foregoing), acceleration, or any other intrinsic or extrinsic characteristics of the camera, the ultrasound probe, the target, or combinations of the foregoing. Similarly, an acquisition state may include environmental factors such as temperature, humidity, air pressure, or the like, as well as operating states of hardware, optics, and so forth. Still more generally, anything that can be monitored or sensed and usefully employed in an ultrasound imaging system as contemplated herein may be used as an acquisition state.

As shown in step 904, capturing acquisition state data may include capturing a pose of the handheld ultrasound probe, which may be performed substantially concurrently with the step of obtaining the ultrasound image, and may include any of the techniques described above. This step may also or instead employ other techniques for measuring position and orientation of an ultrasound probe with respect to a skin surface. For example, the present process may be combined with techniques involving the use of accelerometers or gyroscopes, or techniques involving the level of speckle dissimilarity or decorrelation between consecutive scans.

As shown in step 906, capturing acquisition state data may also or instead include capturing a contact force of the handheld ultrasonic probe, which may be performed substantially concurrently with the step of obtaining the ultrasound image.

As shown in step 908, the process 900 may include normalizing the ultrasound images to a common contact force. As shown in step 910, the process 900 may include storing ultrasound image data and any acquisition state data (e.g., pose and contact force) temporally or otherwise associated therewith. As shown in step 912, the process 900 may include displaying one or more ultrasound images and/or acquisition state data or the like. As shown in step 914, the process 900 may include aligning the ultrasound image(s) in a world coordinate system, such as by using the acquisition state data. As shown in step 916, the process 900 may include reconstructing a volume of the target, or an object or feature within the target, using a plurality of ultrasound images. This may be accompanied by a display of the reconstructed volume. More generally, any use of the various types of acquisition state data described above for control, image enhancements, or other visualizations and/or data processing may be incorporated into the process 900.

Figure 10:
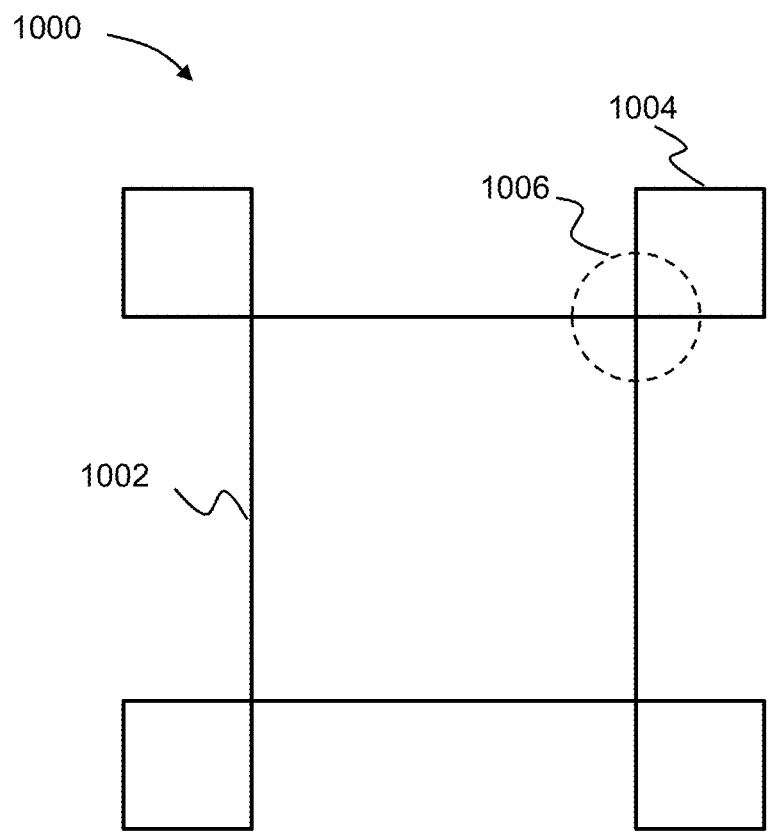
FIG. 10 shows a fiducial marker.

FIG. 10 shows a fiducial marker that may be used with the techniques described above. The fiducial marker 1000 may be applied to a skin surface of a target as a sticker, or using ink or any other suitable marking technique. In one aspect, the fiducial marker 1000 may be black, or any other color or combination of colors easily detectable using digital imaging techniques. In another aspect, the fiducial marker 1000 may be formed of a material or combination of materials transparent to ultrasound so as not to interfere with target imaging. The fiducial marker 1000 may also have a variety of shapes and/or sizes. In one embodiment, the fiducial marker 1000 may include an inner square 1002 of about three millimeters in height, and one or more outer squares 1004 of about one millimeter in height on the corners of the inner square 1002. In this manner, several corner features 1006 are created for detection using an imaging device.

While the systems and methods above describe specific embodiments of acquisition states and uses of same, it will be understood that acquisition state data may more generally be incorporated into an ultrasound imaging workflow, such as to provide operator feedback or enhance images. Thus in one aspect there is disclosed herein techniques for capturing an acquisition state for an ultrasound scan and using the acquisition state to either control an ultrasound probe (such as with force feedback as described above) or to provide user guidance (such as to direct a user through displayed instructions or tactile feedback to a previous acquisition state for a patient or other target). The improved workflows possible with an ultrasound probe that captures acquisition state are generally illustrated in the following figure.

Figure 11:
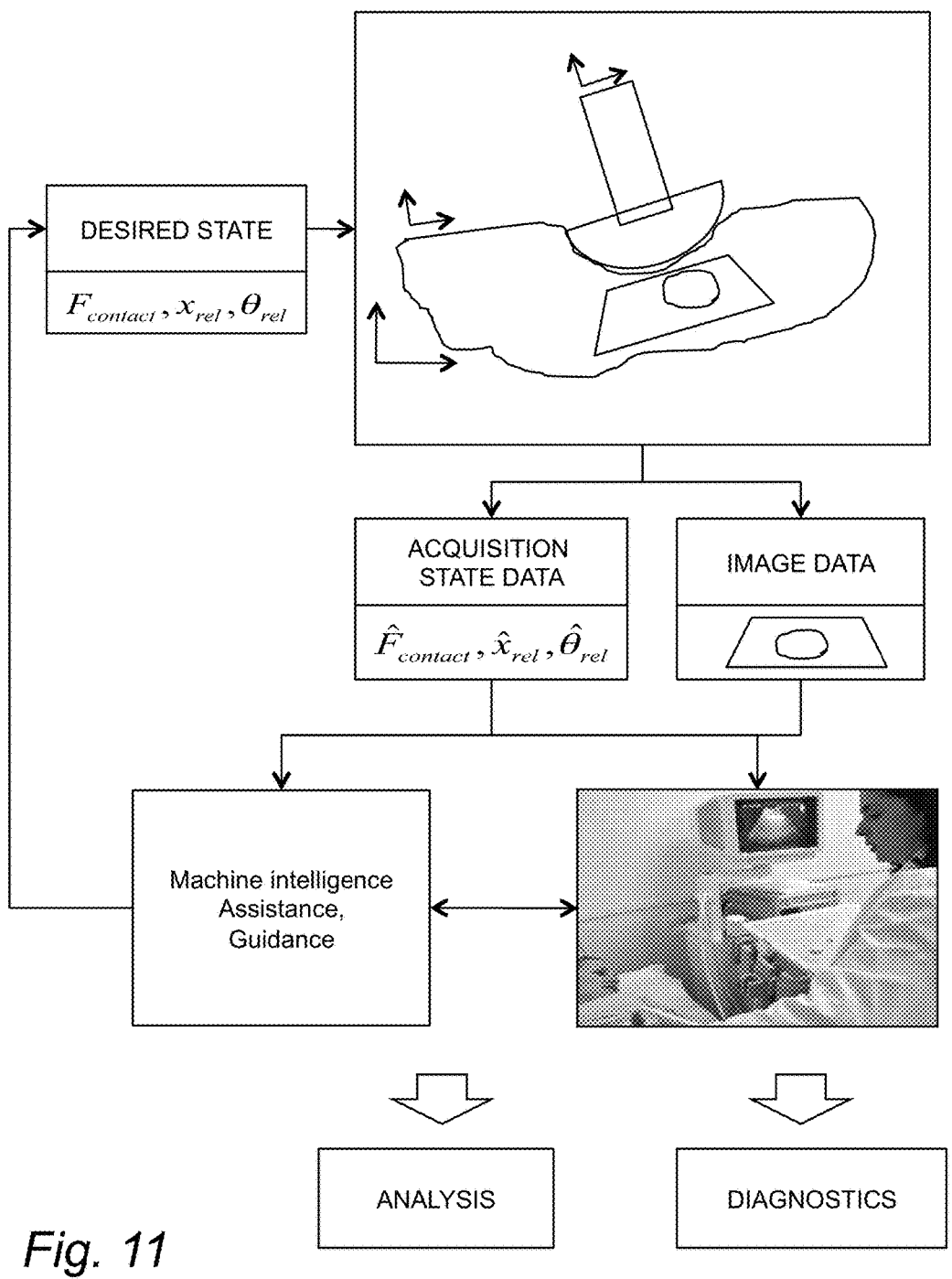
FIG. 11 shows a generalized workflow using acquisition states.

FIG. 11 shows a generalized workflow using acquisition states. In general, an ultrasound probe such as any of the devices described above may capture image data and acquisition state data during an ultrasound scan. In one aspect, this data may be fed directly to a user such as an ultrasound technician during a scan. For example, ultrasound images and/or acquisition state data may be displayed on a display of a computer or the like while a scan is being performed.

In another aspect, machine intelligence may be applied in a variety of manners to augment a scanning process. For example, acquisition state data concerning, e.g., a pose of the ultrasound probe may be used to create a graphical representation of a scanner relative to a target, and the graphical representation may be depicted on the display showing a relative position of the ultrasound probe to the target in order to provide visual feedback to the user concerning orientation. As another example, contact force may be displayed as a numerical value, and/or an ultrasound image with a normalized contact force may be rendered for viewing by the user during the scan. As another example, the contact force may be provided as a visual or audio indication on the probe as further described in FIG. 16. In another aspect, a desired acquisition state may be determined (e.g., provided by a user to the computer), and the machine intelligence may create instructions for the user that can be displayed during the scan to steer the user toward the desired acquisition state. This may be a state of diagnostic significance, and/or a previous acquisition state from a current or historical scan. In another aspect, the desired acquisition state may be transmitted as control signals to the ultrasound probe. For example, control signals for an instantaneous contact force may be communicated to a force-controlled ultrasound device such as the device described above. This may also or instead include scanning data parameters such as frequency or array beam formation, steering, and focusing.

In addition, the capability of capturing a multi-factor acquisition state including, e.g., contact force and position permits enhancements to analysis and diagnostic use of an ultrasound system. For example, analysis may include elastography, image normalization, three-dimensional reconstruction (e.g., using normalized images), volume and/or shape analysis, and so forth. Similarly, diagnostics may be improved, or new diagnostics created, based upon the resulting improved ultrasound images as well as normalization of images and accurate assessment of an acquisition state. All such uses of an ultrasound system having acquisition state capabilities, feedback control capabilities, and machine intelligence as contemplated herein are intended to fall within the scope of this disclosure.

FIG. 12 shows a pyramid. The pyramid 1200, which may be a four-sided pyramid or any other shape, may be used as a convenient and intuitive graphical representation for pose information and instantaneous contact force for an ultrasound probe. When viewed from the top (as shown in FIG. 13), the pyramid appears as a square with an X in the middle. As a perspective on the pyramid 1200 varies, a two-dimensional projection of the pyramid provides visual information concerning relative pose (position, orientation, and in the case of an ultrasound probe, axial rotation). For example, when rotated about an axis passing through the apex of the pyramid 1200, the resulting projection appears rotated as shown in FIG. 14. In order to resolve any rotational ambiguity associated with a projection that has one or more axes of symmetry, each edge of the graphical representation may be rendered in a different color. Thus for example, a first edge 1402 may be rendered in red, a second edge 1404 may be rendered in green, and so forth. Any other suitable technique may be used to visually encode rotational information so that a unique rotational orientation can be determined. For example, one side may be rendered using a heavier line, or include an "x" across the line, a break in the line, an "s" or other distinguishable feature in the line, or any other visualization to uniquely identify a particular one of the edges.

When a position changes, e.g., away from directly above the apex, the projected shape changes in a corresponding fashion, such as along a face as shown in FIG. 15, or along an edge as shown in FIG. 16. More generally, any change in pose relative to the pyramid can result in a corresponding change in the projected shape. This general approach may be used to visually encode a difference between a target pose for an ultrasound probe and a current pose, which may be determined for example using the techniques described above.

FIG. 17 shows a pyramid. In a similar fashion to the perspective changes described above, a scale of a graphical representation 1700 such as a projection of a pyramid may be used to visually encode an instantaneous contact force, or more specifically for a system configured to recover an acquisition state, a difference between a target instantaneous contact force and a current instantaneous contact force for an ultrasound probe. Thus, the graphical representation 1700 shown in FIG. 17 may be smaller than the graphical representation depicted in FIG. 13 when rendered, e.g., in a user interface, thus signifying an instantaneous contact force greater (or smaller, according to user preference or system configuration) than a target contact force.

Thus, as a pose of an ultrasound probe changes, the graphical representation 1700 may transformed, morphed, or otherwise rendered to reflect such changes. Similarly, as the ultrasound probe is rotated about its main axis, the graphical representation 1700 may be rotated. And as an instantaneous contact force applied by the ultrasound probe to a target surface varies, the graphical representation 1700 may be scaled larger and smaller to reflect the contact force. More generally, as the ultrasound probe is operated, the graphical representation 1700 may be altered to provide spatial information concerning the pose (i.e., position and orientation), axial rotation (which may be based upon an axis of the pose coordinate system, or independently tracked as rotation about a normal to the target surface), and instantaneous contact force for the ultrasound probe relative to a target surface.

While such an approach may be used without additional visual elements, the approach may be improved by providing a reference object within the graphical representation 1700 that represents a target pose and/or contact force for an ultrasound probe. For the projected pyramid described above, the reference image may, for example, include a square with an 'X' as shown in FIG. 13. By including this reference image, a user of an ultrasound probe may receive an intuitive visual representation of a difference between a target acquisition state and a current acquisition state of an ultrasound probe operated by the user.

Figure 18:
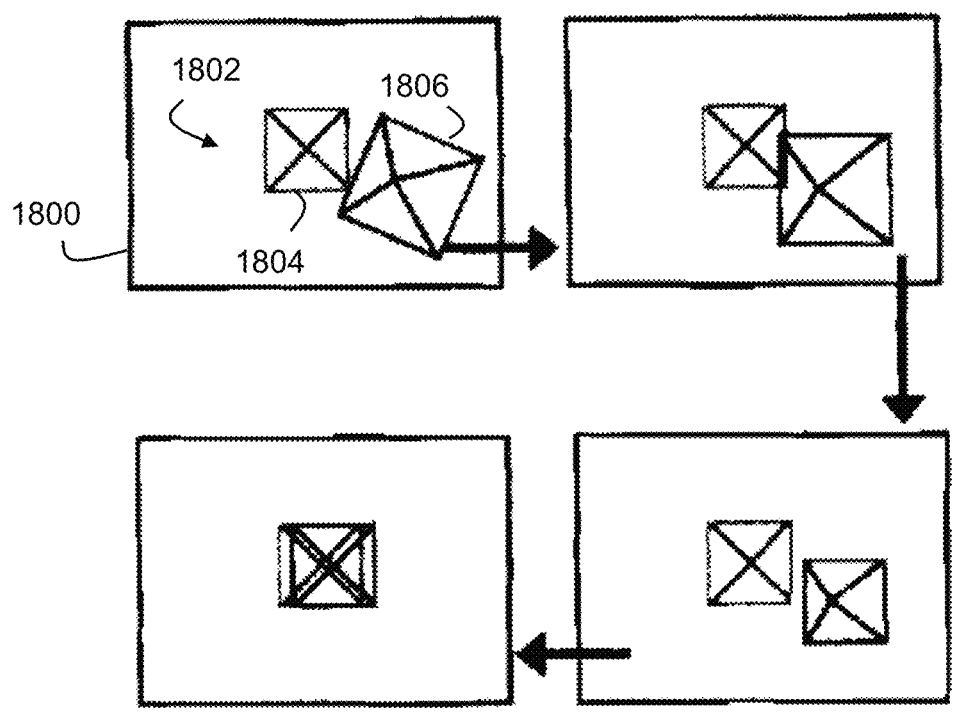
FIG. 18 depicts a display using a graphical representation during user operation of an ultrasound probe.

FIG. 18 depicts a display using a graphical representation during user operation of an ultrasound probe. As described above, the user interface 1800 may display a graphical representation 1802 containing a reference image 1804 and a current image 1806. By seeking to align the current image 1806 with the reference image 1804. In a first step, a user may rotate an ultrasound probe along its access, causing a corresponding rotation of the current image 1806 as shown in a second, updated instance of the user interface 1810. A user may then increase (or decrease) contact force resulting in corresponding changes to a scale of the current image, as generally depicted in a third instance of the user interface 1820. Finally, a user may pivot the ultrasound probe about a point of contact with a target surface, thus bringing the current image 1806 into alignment with the reference image 1804.

The system may determine when the ultrasound probe is suitably aligned with a target pose and contact force. This may, for example, be determined based on quantitative data for the pose and contact force stored in the system, or based upon visual analysis of the current image 1806 and reference image 1804. Thus, for example, the probe may be considered adequately aligned or "substantially" aligned when the reference image 1804 is within three pixels of the current image 1806 throughout. The images may be appropriately scaled so that this visual difference of three pixels within the interface correspondence to a suitable physical alignment of the ultrasound probe to a target acquisition state.

It will be appreciated that, while a pyramid is depicted, any other suitable graphic may be employed for the reference image 1804 and the current image 1806 without departing from the scope of this disclosure, provided such images provide useful visual feedback to a user when operating an ultrasound probe to recover a target acquisition state.

Figure 19:
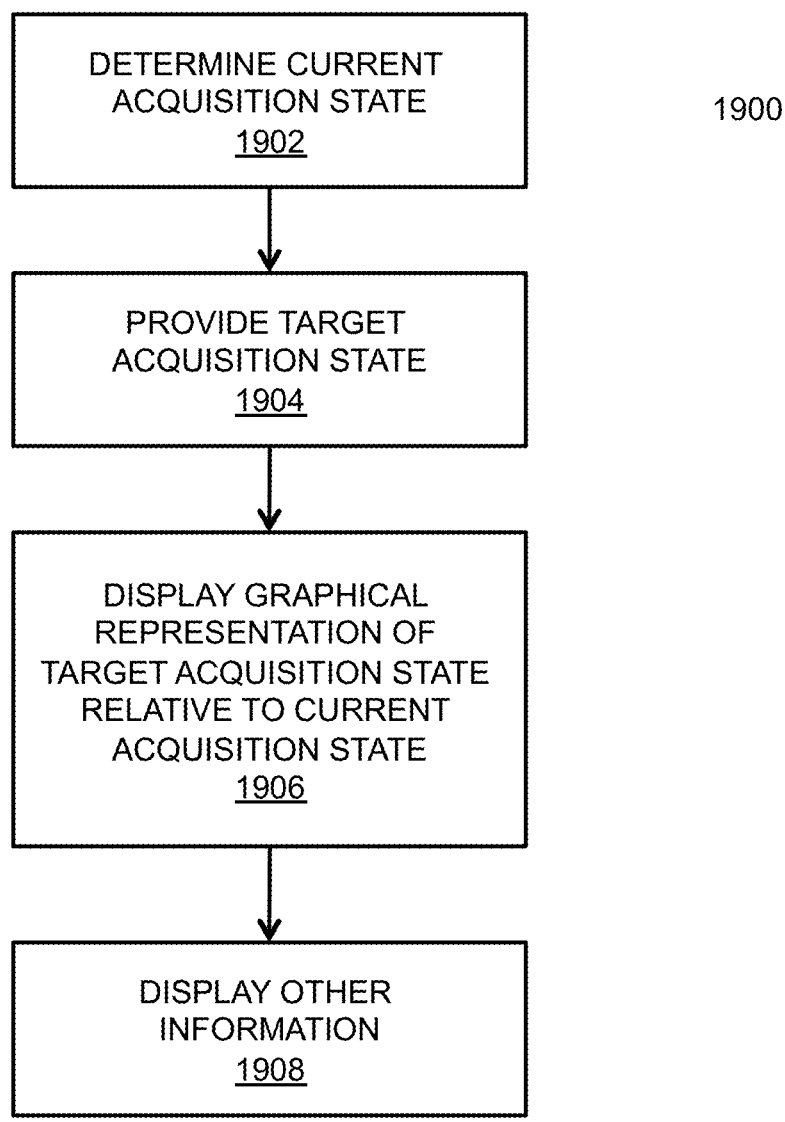
FIG. 19 shows a process for providing visual feedback to a user of an ultrasound probe.

FIG. 19 shows a process for providing visual feedback to a user of an ultrasound probe to recover an acquisition state.

As shown in step 1902, the process 1900 may begin with determining a current acquisition state of the ultrasound probe. The current acquisition state may for example include current pose information and a current instantaneous contact force between the ultrasound probe and a surface, all as generally described above.

As shown in step 1904, the process 1900 may include providing a target acquisition state of the ultrasound probe. The target acquisition state may for example include target pose information and a target instantaneous contact force for the ultrasound probe, which may be referenced to a shared coordinate system with the current acquisition state. It will be readily appreciated that the order of steps 1902 and 1904 is arbitrary, and they may be performed at any suitable frequency and in any suitable order provided that a comparison can be made that provides useful visual feedback to an operator of the ultrasound probe. It should be similarly appreciated that any shared coordinate system may be used, including a coordinate system for the probe, a coordinate system for the target surface, or some other world coordinate system, with transformations between coordinate system being readily achieved by one of ordinary skill in the art.

The target pose information may, for example, include at least one of a target position, a target orientation, and a target rotation for the ultrasound probe. The target pose information may be associated with a previous scan, the target pose information being stored in memory in order to guide a user to a previous scan state, or the target pose information may be manually entered by a user in order to guide a user to a manually selected state. More generally, the target pose information may be any useful reference point to which an ultrasound probe might be directed.

As shown in step 1906, the process 1900 may include displaying a graphical representation of the target acquisition state relative to the current acquisition state. As described above, the graphical representation may include a first graphic or image corresponding to the target acquisition state and a second graphic or image representing the current acquisition state. The second graphic may be geometrically similar to and superimposed on the first graphic for intuitive user interpretation of the display. One of the images may be scaled, skewed, transformed or the like to provide user feedback to recover an acquisition state. For example, the second graphic may be scaled according to a difference between the current instantaneous contact force and the target instantaneous contact force. The second graphic may also or instead be geometrically transformed according to a difference between the current pose information and the target pose information.

The graphical representation may be dynamically adjusted during an ultrasound scan or the like in order to provide real time visual feedback to a user on probe positioning. As noted above, the graphical representation may include a projection of a pyramid, where a projection for the second graphic is the same pyramid varied according to the difference between the current pose information and the target pose information. A variety of other suitable transformations may be employed, such as an affine transformation of the pyramid.

The graphics may visually encode a unique rotational orientation of an ultrasound probe along a main axis using any suitable technique, such as by using different colors along a perimeter of the pyramid (e.g., a different color for each side), or by adding a single, unique feature on one side for visual discrimination.

As shown in step 1908, the process 1900 may include displaying other information. This may, for example, include displaying visual information such as an ultrasound image from the ultrasound probe. This may be a current image, a previous image (e.g., an image associated with the target acquisition state) or any other ultrasound image of interest. The graphical representation may be displayed within the ultrasound image so that a user can view the ultrasound image concurrently with the graphical representation. Other information may also usefully be displayed such as a numerical display of the current instantaneous contact force or the target instantaneous contact force.

Similarly, a visual alert may be provided such as a visual indicator when the current acquisition state is substantially aligned with the target acquisition state. This may, for example, include flashing the graphical representation, changing a color of the visual indicator, changing a brightness of the visual indicator, changing a shade of the visual indicator, and so forth. Other alerts such as auditory feedback (e.g. a beep or buzzer), tactile feedback (e.g., vibration) or the like may also or instead be used to signal to a user when the current acquisition state is substantially aligned with the target acquisition state. More generally, any visual, auditory, or tactile alerts may be suitably employed to provide feedback to a user that supplements the graphical representation within the user interface.

It will be appreciated that many of the above systems, devices, methods, processes, and the like may be realized in hardware, software, or any combination of these suitable for the data processing, data communications, and other functions described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the handheld probe and a remote desktop computer or storage device, or all of the functionality may be integrated into a dedicated, standalone device including without limitation a wireless, handheld ultrasound probe. All such permutations and combinations are intended to fall within the scope of the present disclosure.

In other embodiments, disclosed herein are computer program products comprising computer-executable code or computer-usable code that, when executing on one or more computing devices (such as the controller described above), performs any and/or all of the steps described above. The code may be stored in a computer memory or other non-transitory computer readable medium, which may be a memory from which the program executes (such as internal or external random access memory associated with a processor), a storage device such as a disk drive, flash memory or any other optical, electromagnetic, magnetic, infrared or other device or combination of devices. In another aspect, any of the processes described above may be embodied in any suitable transmission or propagation medium carrying the computer-executable code described above and/or any inputs or outputs from same.

It should further be appreciated that the methods above are provided by way of example. Absent an explicit indication to the contrary, the disclosed steps may be modified, supplemented, omitted, and/or re-ordered without departing from the scope of this disclosure.

The method steps of the invention(s) described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps.

While particular embodiments of the present invention have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method for providing feedback to an ultrasound probe user to recover an acquisition state, the method comprising:
determining a current acquisition state of the ultrasound probe, the current acquisition state including current pose information for a current pose of the ultrasound probe relative to an object and further including a current instantaneous contact force between the ultrasound probe and a surface of the object;
providing a target acquisition state of the ultrasound probe, the target acquisition state including target pose information;
displaying a graphical representation of the target acquisition state relative to the current acquisition state, wherein the graphical representation includes a first graphic corresponding to the target acquisition state and a second graphic representing the current acquisition state, the second graphic geometrically similar to and superimposed on the first graphic, wherein the second graphic is geometrically transformed according to a difference between the current pose and the target pose information;
obtaining a first ultrasound image from the ultrasound probe at the current pose and the current instantaneous contact force when the current pose is at or near the target pose; and
normalizing the first ultrasound image to an estimate of the first ultrasound image at the current pose and a predetermined contact force different than the current instantaneous contact force and greater than zero Newton, wherein normalizing the first ultrasound image includes using a trajectory field that characterizes a displacement of one or more features within the first ultrasound image according to variations in a contact force applied by the ultrasound probe to the surface, thereby providing a normalized ultrasound image; and
displaying the normalized ultrasound image to a user.

2. The method of claim 1 wherein the target pose information includes at least one of a target position, a target orientation, and a target rotation for the ultrasound probe.

3. The method of claim 1 further comprising dynamically adjusting the graphical representation during an ultrasound scan with the ultrasound probe.

4. The method of claim 1 wherein the graphical representation includes a projection of a pyramid, and wherein the projection for the second graphic is varied according to the difference between the current pose information and the target pose information.

5. The method of claim 1 wherein the second graphic is geometrically transformed using an affine transformation.

6. The method of claim 1 wherein the second graphic visually encodes a unique rotational orientation.

7. The method of claim 6 wherein the unique rotational orientation is selected according to a difference between a target rotation and a current rotation of the ultrasound probe about an axis of the ultrasound probe.

8. The method of claim 6 wherein the first graphic and the second graphic each include a perimeter displayed in a plurality of different colors to visually encode rotational orientation.

9. The method of claim 1 wherein the target acquisition state is an acquisition state associated with a previous scan.

10. The method of claim 1 wherein the target acquisition state is manually entered by a user.

11. The method of claim 1 further comprising displaying a current ultrasound image from the ultrasound probe.

12. The method of claim 11 further comprising displaying the graphical representation within the displayed current ultrasound image.

13. The method of claim 1 further comprising numerically displaying the current instantaneous contact force for the ultrasound probe.

14. The method of claim 13 wherein the target acquisition state includes a target instantaneous contact force, the method further comprising numerically displaying the target instantaneous contact force for the ultrasound probe.

15. The method of claim 1 further comprising providing a visual indicator to a user when the current acquisition state is substantially aligned with the target acquisition state.

16. The method of claim 15 wherein the visual indicator includes flashing the graphical representation.

17. The method of claim 15 wherein the visual indicator includes changing at least one of a color or a shade of the graphical representation.

18. The method of claim 15 further comprising providing at least one of auditory feedback and tactile feedback when the current acquisition state is substantially aligned with the target acquisition state.

19. The method of claim 1 further comprising combining a plurality of ultrasound images from a plurality of different poses, each normalized to the predetermined contact force, into a volumetric reconstruction of the object.

20. The method of claim 1 wherein the target acquisition state includes a target instantaneous contact force, and wherein the second graphic is scaled according to a difference between the current instantaneous contact force and the target instantaneous contact force.

21. A device comprising:
an ultrasound probe including one or more ultrasound transducers to capture an ultrasound image of a target through a skin surface;
a sensor system configured to obtain current pose information for a current pose of the ultrasound probe relative to the skin surface;
a force sensor configured to obtain a current instantaneous contact force between the ultrasound probe and the skin surface;
a memory that stores a current acquisition state and a target acquisition state for the ultrasound probe, the target acquisition state including target pose information and the current acquisition state including the current pose information and the current instantaneous contact force;
a processor configured to generate a graphical representation of a difference between the target acquisition state and the current acquisition state, the processor further configured to process a first ultrasound image obtained from the ultrasound probe at the current pose and the current instantaneous contact force when the current pose is at or near the target pose by normalizing the first ultrasound image to an estimate of the first ultrasound image at the current pose and a predetermined contact force different than the current instantaneous contact force and greater than zero Newton, wherein normalizing the first ultrasound image includes using a trajectory field that characterizes a displacement of one or more features within the first ultrasound image according to variations in a contact force applied by the ultrasound probe to the skin surface, thereby providing a normalized ultrasound image for viewing by a user; and
a display coupled to the processor to display the graphical representation and one or more of the first ultrasound image and the normalized ultrasound image for a user of the ultrasound probe.

22. The device of claim 21, wherein the display is configured to display a current ultrasound image from the ultrasound probe.

23. A method for providing feedback to an ultrasound probe user to recover an acquisition state, the method comprising:
determining a current acquisition state of the ultrasound probe, the current acquisition state including a current pose of the ultrasound probe relative to an object and further including a current instantaneous contact force between the ultrasound probe and a surface of the object;
providing a target acquisition state of the ultrasound probe, the target acquisition state including a target pose for capturing a region of interest within the object;
displaying a graphical representation providing user feedback to direct a user to steer the ultrasound probe to the target pose;
obtaining a first ultrasound image from the ultrasound probe at the current pose and the current instantaneous contact force when the current pose is at or near the target pose;
normalizing the first ultrasound image to an estimate of the first ultrasound image at the current pose and a predetermined contact force different than the instantaneous contact force and greater than zero Newton, wherein normalizing the first ultrasound image includes using a trajectory field that characterizes a displacement of one or more features of the object within the first ultrasound image according to variations in a contact force applied by the ultrasound probe to the surface of the object, thereby providing a normalized ultrasound image; and
displaying the normalized ultrasound image to a user.

24. The method of claim 23 further comprising combining a plurality of ultrasound images from a plurality of different poses, each normalized to the predetermined contact force, into a volumetric reconstruction of the object.

25. The method of claim 24 wherein displaying the normalized ultrasound image includes displaying the volumetric reconstruction of the object.

* * * * *